US011458125B2

(12) United States Patent
Crutchley

(10) Patent No.: US 11,458,125 B2
(45) Date of Patent: *Oct. 4, 2022

(54) TOPICAL COMPOSITION COMPRISING TACROLIMUS

(71) Applicant: MC2 Therapeutics Limited, Letherhead (GB)

(72) Inventor: Nigel Crutchley, Letherhead (GB)

(73) Assignee: MC2 Therapeutics Limited, Leatherhead (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/090,993

(22) PCT Filed: Apr. 3, 2017

(86) PCT No.: PCT/EP2017/057897
§ 371 (c)(1),
(2) Date: Oct. 3, 2018

(87) PCT Pub. No.: WO2017/174530
PCT Pub. Date: Oct. 12, 2017

(65) Prior Publication Data
US 2019/0060288 A1    Feb. 28, 2019

(30) Foreign Application Priority Data

Apr. 4, 2016  (EP) .................................. 16163724

(51) Int. Cl.
*A61K 31/436* (2006.01)
*A61K 47/14* (2017.01)
*A61K 9/107* (2006.01)
*A61K 47/06* (2006.01)
*A61K 9/00* (2006.01)
*A61P 17/06* (2006.01)

(52) U.S. Cl.
CPC .......... *A61K 31/436* (2013.01); *A61K 9/0014* (2013.01); *A61K 9/107* (2013.01); *A61K 47/06* (2013.01); *A61K 47/14* (2013.01); *A61P 17/06* (2018.01)

(58) Field of Classification Search
CPC .... A61K 31/436; A61K 9/0014; A61K 9/107; A61K 47/14
See application file for complete search history.

(56) References Cited

U.S. PATENT DOCUMENTS

| 4,486,333 | A | 12/1984 | Sebba |
| 8,574,563 | B2 | 11/2013 | Bachand et al. |
| 2005/0232869 | A1 | 10/2005 | Tamarkin et al. |
| 2005/0249757 | A1 | 11/2005 | Kannan et al. |
| 2007/0276004 | A1* | 11/2007 | Hirsch .................. A61K 31/436 514/330 |
| 2009/0137523 | A1 | 5/2009 | Shin et al. |
| 2009/0221625 | A1 | 9/2009 | Hirsch et al. |
| 2011/0201639 | A1 | 8/2011 | Skak et al. |
| 2012/0184511 | A1 | 7/2012 | Goebel |

FOREIGN PATENT DOCUMENTS

| EA | 200600139 | 8/2006 |
| EP | 0474126 A1 | 3/1992 |
| EP | 1093371 | 5/2005 |
| EP | 2308468 A1 | 4/2011 |
| EP | 2596788 A1 | 5/2013 |
| JP | H10-508588 A | 8/1998 |
| JP | 2006522059 A | 9/2006 |
| JP | 2013507337 A | 3/2013 |
| WO | WO 97/32559 A1 | 9/1997 |
| WO | WO 03/064024 A1 | 8/2003 |
| WO | WO 2005/082515 A2 | 9/2005 |
| WO | WO 2006/062334 A1 | 6/2006 |
| WO | WO 2006/099390 A1 | 9/2006 |
| WO | WO 2009/001092 A1 | 12/2008 |
| WO | WO 2009/001099 A2 | 12/2008 |
| WO | WO 2009/090495 A2 | 7/2009 |
| WO | 2010/096868 A1 | 9/2010 |
| WO | 2012/011566 A1 | 1/2012 |

OTHER PUBLICATIONS

First Examination Report from Indian Patent Application No. 201847040549, dated Nov. 25, 2019.
Yamanaka et al., "Development and evaluation of a tacrolimus cream formulation using a binary solvent system", International Journal of Pharmaceuticals, (2014).
Jayaraman et al., "Topical Delivery of Erythromycin from Various Formulations: An In Vivo Hairless Mouse Study", Journal of Pharmaceutical Sciences (1996) vol. 85(10): 1082-1084.
International Search Report and Written Opinion for PCT/EP2017/057897 dated Jun. 8, 2017.
Search Report for European Patent Application No. 16163724.4, dated Sep. 19, 2016.
International Preliminary Report on Patenatbility for PCT/EP2017/057897, dated Oct. 9, 2018.
G. Godwin, Harry's Cosmetology 7th Edition (1982).
Mollison et al., "A macrolactam inhibitor of T helper type 1 and T helper type 2 cytokine biosynthesis for topical treatment of inflammatory skin diseases", J Invest Dermatol., 112(5):729-38 (1999).
Sebba, "Biliquid Foams—A Preliminary Report", J. Colloid and Interface Science, 40:2, 468-474 (1972).
Sebba, "The Behaviour of Minute Oil Droplets Encapsulated in a Water Film", Colloid Polymer Sciences, 257, 392-396 (1979).
Hicks, "Investigating the Generation, Characterisation Structure of Biliquid Foams", PhD Thesis, University of Bristol (2005).
Crutchley, "The Encapsulation of Oils and Oil Soluble Substances Within Polymer Films", PhD Thesis, The University of Leeds (2006).
Lye and Stuckey, "Structure and stability of colloidal liquid aphrons," Colloid and Surfaces, 131, 119-136 (1998).

(Continued)

*Primary Examiner* — Shobha Kantamneni
(74) *Attorney, Agent, or Firm* — Merchant & Gould P.C.

(57) ABSTRACT

The present invention relates to a composition for topical application comprising: a first discontinuous phase comprising a first oil and tacrolimus; a second discontinuous phase comprising a second oil; and a continuous aqueous phase; wherein the first oil is different from the second oil.

18 Claims, 8 Drawing Sheets

(56) References Cited

OTHER PUBLICATIONS

Figure 1:
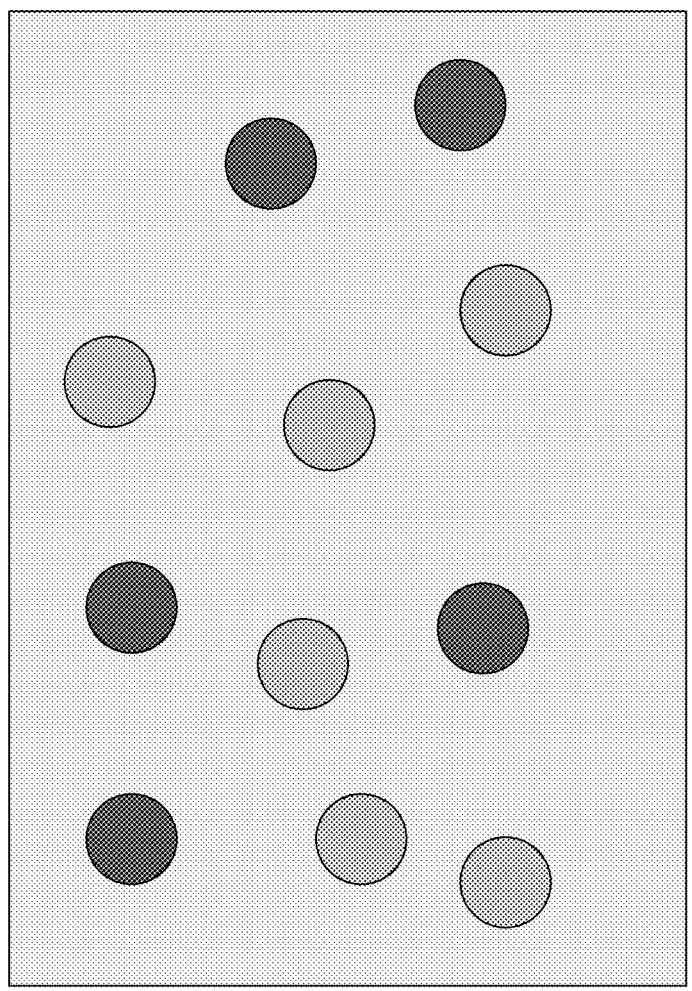

Japanese Examination Report for JP Application No. 2019-502155 dated Mar. 23, 2021—English Translation provided (6 pages).
Indian Hearing Notice for IN Application No. 201847040549 dated Sep. 9, 2021 (3 pages).
Chinese Examination Report for CN Application No. 201780026171.3 dated Jun. 28, 2021—English Translation provided (6 pages).
Remitz et al. "Tacrolimus ointment improves psoriasis in a microplaque assay." British Journal of Dermatology, vol. 141. (1999) pp. 103-107.

* cited by examiner

TOPICAL COMPOSITION COMPRISING TACROLIMUS

This application is a National Stage Application of PCT/EP2017/057897, filed 3 Apr. 2017, which claims the benefit of priority to European Patent Application No. 16163724.4, filed 4 Apr. 2016, which applications are incorporated herein by reference. To the extent appropriate, a claim of priority is made to each of the above disclosed applications.

The present invention relates to a topical composition. In particular, the invention relates to a topical composition comprising tacrolimus having improved skin permeation, stability and patient compliance.

Atopic dermatitis is a common, chronically relapsing, inflammatory skin disease. The exact cause of the disease is a matter of debate but it is characterised by eczematous lesions, dry skin and intense pruritus (itching). There is also strong evidence that the prevalence of atopic dermatitis has been increasing over recent years. The condition can vary from mild to severe with subsequent detriment to quality of life.

Current treatment programs include the use of emollient creams and then supplementing this with other therapies on a graduated scale. Topical application of a mild corticosteroid such as hydrocortisone acetate is usually the next step, with increasingly potent corticosteroids being utilised only if necessary. There are, however, a number of potential drawbacks associated with topical corticosteroids. These drawbacks, which apply especially to the more potent corticosteroids, can include skin thinning, tachyphylaxis and rebound phenomena. Due to these and other potential side effects, corticosteroids are not advised for use on the facial areas. This is despite the fact that atopic dermatitis that develops on the face can be the most detrimental to a patient's quality of life.

Recently, topically applied macrolactam immunosuppressives have been used for treating moderate to severe atopic dermatitis. Unlike corticosteroids, these compounds generally have a good tolerance profile and and so can be used on the facial areas.

Tacrolimus belongs to the ascomycin class of macrolactam immunosuppressives. Mechanistically, tacrolimus does not directly inhibit a cellular process but instead forms a complex with the specific cytoplasmic protein cis-trans prolyl isomerase FKBP12 (also known as FK506 binding protein), a member of the immunophilin protein family. It is this resultant complex that subsequently inhibits the inflammatory response.

In the case of tacrolimus the derived complex inhibits calcineurin, preventing the dephosphorylation of the nuclear factor of activated T-cells (NF-AT) and thereby decreasing the activity of genes coding for IL-2 and related cytokines within those cells.

While tacrolimus presents clear advantages over corticosteroids in terms of its tolerance profile, formulating tacrolimus for topical application has proved challenging. A first difficulty that arises is obtaining a chemically and physically stable product. A second difficulty that arises is managing to deliver a sufficient amount of the active through the outer skin barrier for it to be efficacious. Permeation of tacrolimus is hindered by its molecular size (804 Da), which is far greater than the commonly recognised readily permeable size of 500 Da. While the disease state impairs the skin barrier to some extent, there remains a need for strategies to improve the permeation of tacrolimus into the skin.

Commercially, 0.03% and 0.1% tacrolimus anhydrous ointments (Protopic™ by Astellas) have been released. Both commercial products contain a polar solvent (propylene carbonate) dispersed within a liquid paraffin, white soft paraffin, hard paraffin and beeswax medium. The propylene carbonate acts as a carrier and permeation enhancer for the drugs. While the solvent serves to deliver the tacrolimus to the deeper skin layers, it further disrupts the already-compromised skin barrier and therefore causes irritation to the skin. The absence of water limits the chances of chemical degradation due to hydrolysis or pH incompatibility and the occlusive nature of the bulk of the excipients creates a high degree of occlusion aiding permeation of the active. However, like most ointments, the lack of water and the presence of paraffin and wax components give the formulations a very poor aesthetic profile (S. E. Wolverton, Comprehensive Dermatologic Drug Therapy $3^{rd}$ Edition (2012), p13). This can severely limit patient compliance.

Several non-ointment tacrolimus formulations are known. For example, US 2005/0249757 discloses a pharmaceutical cream composition comprising a macrolide immunosuppressant, one or more cream-forming agents, and an effective amount of one or more skin penetration enhancers.

US 2012/0184511 discloses a liquid microemulsion of a macrolide immunosuppressant. The compositions include high levels of surfactants and polar water-miscible liquids as permeation enhancers.

EP 2596788 discloses an oil-in-water type creamy composition comprising tacrolimus in which diisopropyl sebacate may be used in the oil phase. The long-term stability of the composition at elevated temperatures (e.g. 40° C.) is not disclosed.

While the known non-ointment formulations are likely to have a better aesthetic profile than the Protopic™ formulations, they tend to lack the same chemical stability of the active. Moreover, in order to achieve sufficient permeation of the active, it is typically necessary to include a high amount of surfactant and/or polar water-miscible liquid. This is exemplified by US 2005/0249757, US 2012/0184511, and EP 2596788. As a result of the high amount of these components, these non-ointment formulations tend to be irritating to the skin.

Accordingly, it is one object of the present invention to provide a formulation that can deliver tacrolimus into the skin with better aesthetics than prior art formulations, while being as benign as possible the skin barrier. In other words, it is one object of the present invention to provide a tacrolimus formulation having better patient compliance than prior art formulations.

It is an alternative and/or additional object to provide a tacrolimus formulation having better skin penetration than prior art formulations or at least provide a commercially useful alternative thereto.

It is an alternative and/or additional object to provide a formulation that presents improved chemical stability of the tacrolimus in comparison with existing formulations.

According to a first aspect, the present invention provides a composition for topical application comprising:
  a first discontinuous phase comprising a first oil and tacrolimus;
  a second discontinuous phase comprising a second oil; and
  a continuous aqueous phase;
  wherein the first oil is different from the second oil.

The present inventors have found that the compositions disclosed herein, unlike the non-ointment formulations of the prior art, do not require high levels of polar water-miscible liquids or high levels of surfactants to achieve good skin penetration. This presents a number of advantages.

Firstly, the composition is less irritating to the skin, providing improved patient compliance. This is especially advantageous where the patient already has inflamed skin. Secondly, the composition has excellent efficacy in vivo as tested in a porcine inflammatory model. Moreover, the tacrolimus surprisingly has a higher chemical stability than in many existing formulations, especially non-ointment formulations. This will be explained in more detail below.

The present invention will now be described further. In the following passages different aspects/embodiments of the invention are defined in more detail. Each aspect/embodiment so defined may be combined with any other aspect/embodiment or aspects/embodiments unless clearly indicated to the contrary. In particular, any feature indicated as being preferred or advantageous may be combined with any other feature or features indicated as being preferred or advantageous.

The present invention provides a composition for topical application. A composition for topical application is defined herein as a composition that is suitable for direct application to a part of the human or animal body. Preferably, the composition is suitable for direct application to the skin, for example the face, scalp, feet, limbs or trunk.

The composition of the present invention comprises a first discontinuous phase, a second discontinuous phase and a continuous aqueous phase. In other words, the composition comprises a dispersion of a first discontinuous phase and a second discontinuous phase in a continuous aqueous phase. The term "discontinuous phase" as used herein refers to the plurality of discrete regions of the oil droplets that form that particular oil phase. It is not used to refer to a single oil droplet. The phases are physically and chemically distinct. It is to be understood that the first discontinuous phase is not dispersed in the second discontinuous phase, or vice versa. In other words, the composition does not contain a complex internal phase, for example as disclosed in WO 2005/082515. A simple schematic diagram showing the structure of a composition in accordance with the present invention is provided in FIG. 1. The inclusion of a continuous aqueous phase in the present composition enables it to be provided in the form of a lotion or cream, as opposed to an ointment. Thus, the present composition has an improved aesthetic profile relative to the ointments of the prior art, thereby improving patient compliance. Preferably, the composition is in the form of a lotion or cream.

The first discontinuous phase and the second discontinuous phase comprise a first oil and a second oil respectively. The first oil is different from, that is, chemically distinct from, the second oil. Preferably, the first oil and/or the second oil is a pharmaceutically acceptable oil. Examples of oils which may be used in the present invention include coconut oil, squalane, isopropyl myristate, isopropyl isostearate, isopropyl palmitate, modified triglycerides, caprylic capric glycerides, fractionated triglycerides, glyceryl tricaprate, glyceryl tricaproate, glyceryl tricaprylate, glyceryl tricaprylate/caprate, glyceryl tricaprylate/caprate, glyceryl tricaprylate/caprate/laurate, glyceryl tricaprylate/caprate/linoleate, glyceryl tricaprylate/caprate/stearate, glyceryl trilaurate, glyceryl trilinoleate, glyceryl trilinolenate, glyceryl trioleate, glyceryl triundecanoate, linoleic glycerides, saturated polyglycolized glycerides, synthetic medium chain triglyceride containing primarily $C_8$-$C_{12}$ fatty acid chains, medium chain triglycerides, long chain triglycerides, modified triglycerides, fractionated triglycerides, isostearyl isostearate, diisopropyl adipate, mineral oil, dimethicone, cyclomethicone, hydrogenated polyisobutene, heptamethylnonane, and mixtures thereof. Preferably, the composition does not comprise a wax component that is solid at 25° C.

It is to be understood that the first oil and the second oil form two distinct discontinuous phases. In certain exemplary embodiments, the first oil and the second oil are substantially immiscible. Nevertheless, it is equally possible to form two distinct discontinuous phases from two miscible or at least partially miscible oils. This can be achieved by dispersing the first oil and second oil individually in the continuous phase without pre-mixing the oils. Preferably, the first discontinuous phase does not comprise the second oil, and the second discontinuous phase does not comprise the first oil.

The first discontinuous phase comprises tacrolimus. It is to be understood that the term "tacrolimus" encompasses both anhydrous tacrolimus and tacrolimus hydrate. Tacrolimus is a macrolide and belongs to the polyketide class of natural products. It is an immunosuppressant and is known to treat skin conditions. The source of tacrolimus used in the present invention is preferably anhydrous tacrolimus, although it will be appreciated that other sources of tacrolimus may be used, such as tacrolimus hydrate. The amounts of tacrolimus to be incorporated into the compositions based herein are based on the anhydrous form of tacrolimus. It would be within the capabilities of the skilled person to adjust the quantity used in the preparation of the composition depending on the source used to provide the desired amount in the final composition.

Preferably, the first oil comprises diisopropyl adipate. As is shown in the Examples, diisopropyl adipate, diethyl sebacate and dibutyl adipate all have a similar solubility profile for tacrolimus. However, the inclusion of diisopropyl adipate as part of the first oil surprisingly results in significantly higher tacrolimus chemical stability than when diethyl sebacate or dibutyl adipate are included. Without wishing to be bound by theory, it is thought that the two ester linkages present in all three oils are protected more in diisopropyl adipate by steric hindrance caused by proximity/conformation of the methyl groups close to the bond. It is thought that degradation of this bond may subsequently impact the stability of the active, thus explaining the increased stability when diisopropyl adipate is included. It is advantageous for the first discontinuous phase to comprise an oil having a high solvency potential for the tacrolimus because this allows the amount of the first oil to be limited for a given overall tacrolimus concentration. Because the compositions disclosed herein contain two discontinuous phases, using an oil with a poor solvency potential for tacrolimus in the first discontinuous phase would result in a high overall oil content for the formulation, giving poor, greasy aesthetics. The amount of the first oil has a significant bearing on the overall oil level of the formulation where the first and second oils are used in the preferred ratios. Preferably, the composition comprises less than 1 wt % diethyl sebacate and/or less than 1 wt % dibutyl adipate. Preferably, the composition does not comprise diethyl sebacate and/or does not comprise dibutyl adipate.

Another oil that has a good solubility profile for tacrolimus is ethylene glycol salicylate. This oil is frequently used in prior art systems. However, the present inventors have found that the physical stability of the present compositions is significantly higher when diisopropyl adipate is used than ethylene glycol salicylate. Without wishing to be bound by theory, it is thought that diisopropyl adipate, which has a higher logP than ethylene glycol salicylate and is therefore less "polar", has less of a tendency to partition into the aqueous phase. Preferably, the composition comprises less than 1 wt % ethylene glycol salicylate by weight of the composition. More preferably, the composition does not comprise ethylene glycol salicylate.

Preferably, in addition to the diisopropyl adipate, the first oil comprises caprylic capric triglycerides in combination with isopropyl myristate and/or isopropyl palmitate. Alternatively, the first oil may comprise castor oil and/or squalane in addition to the diisopropyl adipate. These oils increase the viscosity of the diisopropyl adipate, thus improving its processability. They may also improve the physical stability of the composition especially when low levels of surfactant are used. Preferably, the first oil comprises and/or consists of diisopropyl adipate and/or isopropyl myristate and/or caprylic capric triglycerides.

The present inventors have additionally found that caprylic capric triglycerides and/or isopropyl myristate have a reasonable solubility profile for tacrolimus as well as providing an emollient function. Thus, it is especially preferred that the first oil comprises and/or consists of diisopropyl adipate in combination with caprylic capric triglycerides and/or isopropyl myristate.

Preferably, the first oil comprises from 10 to 40 wt % diisopropyl adipate and/or from 10 to 40 wt % isopropyl myristate and/or from 20 to 80 wt % caprylic capric triglycerides, by weight of the first oil. More preferably still, the first oil comprises from 20 to 30 wt % diisopropyl adipate and/or from 20 to 30 wt % isopropyl myristate and/or from 40 to 60 wt % caprylic capric triglycerides, by weight of the first oil. Preferably, the first oil consists of diisopropyl adipate and/or isopropyl myristate and/or caprylic capric triglycerides, preferably in the aforementioned amounts.

Preferably, the second oil comprises or consists of an emollient oil, more preferably an oil selected from the group consisting of mineral oil, dimethicone, cyclomethicone, hydrogenated polyisobutane, heptamethylnonane and mixtures of two or more thereof. Most preferably, the second oil comprises or consists of mineral oil. The second oil contributes to the emollient properties of the formulation as well as providing an occlusive layer to promote diffusion of the tacrolimus. As such, the diffusion properties of the composition are enhanced. Preferably, the tacrolimus is substantially insoluble in the second oil. In other words, the second oil preferably acts as a non-solvent oil phase.

Preferably, the first discontinuous phase comprises the first oil in an amount of at least 90 wt % by weight of the first discontinuous phase, more preferably at least 95 wt %, still more preferably at least 97.5 wt % and most preferably at least 99 wt %. Preferably, the first discontinuous phase comprises at most 99.75 wt % of the first oil by weight of the first discontinuous phase. Preferably, the first discontinuous phase comprises tacrolimus in an amount of 0.025 to 10 wt % by weight of the discontinuous phase, more preferably from 0.05 to 5 wt %, still more preferably from 0.25 to 2.5 wt %, and most preferably about 0.5 wt %. Preferably, the first discontinuous phase consists of the first oil and tacrolimus, more preferably in the aforementioned amounts.

Preferably, the second discontinuous phase comprises the second oil in an amount of at least 90 wt % by weight of the second continuous phase, more preferably at least 95 wt %, still more preferably at least 99 wt % and most the second discontinuous phase consists of the second oil.

Preferably, the tacrolimus is predominantly in the first discontinuous phase. By predominantly in the first discontinuous phase it is meant that at least 90 wt % of the tacrolimus is in the discontinuous phase, preferably at least 95 wt %, and more preferably at least 99 wt %. This property of the composition arises as a result of using one or more oils in the first discontinuous phase that have a good solubility profile for the tacrolimus, and a non-solvent oil in the second discontinuous phase. Preferably, the tacrolimus is substantially soluble in the first oil and/or substantially insoluble in the second oil. By substantially soluble is meant having a solubility of at least 0.1 wt % at 25° C., preferably at least 0.2 wt %. By substantially insoluble is meant having a solubility of less than 0.1 wt % at 25° C., preferably less than 0.05 wt %.

As a result of the choice of oil phases, the continuous aqueous phase of the present invention does not need to include high levels of polar water-miscible liquids, such as alcohols and glycols, in order to achieve effective skin penetration or solvation of the tacrolimus. These liquids are typically required as permeation enhancers in conventional tacrolimus formulations. Preferably, the composition of the present invention comprises less than 10 wt % by weight of the composition of $C_1$-$C_4$ alcohols, polyethylene glycol, ethylene glycol, propylene glycol, butylene glycol, pentylene glycol, glycerol, diethylene glycol mono ethyl ether, propylene carbonate or mixtures thereof. In other words, these components do not need to be present in the composition, but where one or more of them is present, the total amount of these components is less than 10 wt % by weight of the composition. More preferably, the composition comprises less than 5 wt % by weight of the composition of $C_1$-$C_4$ alcohols, polyethylene glycol, ethylene glycol, propylene glycol, butylene glycol, glycerol, diethylene glycol mono ethyl ether, propylene carbonate or mixtures thereof, still more preferably less than 2 wt %, still more preferably less than 1 wt %, still more preferably less than 0.5 wt %, still more preferably less than 0.2 wt %, and most preferably less than 0.1 wt % by weight of the composition. Preferably, these compounds are not present in the composition.

The use of only low levels of polar water-miscible liquids (or none at all) is facilitated by the use of the first and second discontinuous phases described herein and minimises the skin irritancy caused by the composition. This is especially advantageous where the patient already has inflamed skin. The fact that such low levels of polar water-miscible liquids can be used is surprising because tacrolimus formulations, and in particular the non-ointment formulations, typically need high levels of these solvents to act as a permeation enhancer.

Preferably, the composition of the present invention comprises a surfactant. The surfactant may be incorporated into one or more of the discontinuous phases and/or the continuous aqueous phase. Suitable surfactants include an alkyl polyglycol ether, an alkyl polyglycol ester, an ethoxylated alcohol, a polyoxyethylene sorbitan fatty acid ester, a polyoxyethylene fatty acid ester, an ionic or non-ionic surfactant, a hydrogenated castor oil/polyoxyethylene glycol adduct containing from 25 to 60 ethoxy groups, a castor oil/polyoxyethylene glycol adduct containing from 25 to 45 ethoxy groups, a sorbitan fatty acid ester (for example Span 20 or Span 80), a block copolymer of ethylene oxide and propylene oxide (for example Pluronic L121 or Pluronic F68), or a mixture thereof. Alternatively polymeric surfactants based on modified crosslinked copolymers of acrylic acid such as Pemulen Tr-1 and Pemulen Tr-2 (Lubrizol Corporation) could be used. It will be understood that other suitable surfactants may be used.

Preferably, the composition comprises two or more surfactants, for example a first surfactant incorporated into the first and/or second discontinuous phases, and a second, different surfactant incorporated into the continuous aqueous phase. The first and second surfactants are preferably selected from the list above. The first surfactant readily dissolves or disperses in the first and/or second oil and is preferably selected from the group consisting of Laureth-4 (polyoxyethylene (4) monododecyl ether), polysorbate 80, Span 80, and mixtures of two or more thereof. The second surfactant readily dissolves or disperses in the continuous aqueous phase and is preferably selected from the group consisting of Polysorbate 20, Pluronic L121, Pluronic F68, PEG-40 hydrogenated castor oil, Span20 and mixtures of two or more thereof. Most preferably, the first surfactant is Laureth-4 (polyoxyethylene (4) monododecyl ether), and the second surfactant is Polysorbate 20.

Alternatively, the composition may comprise only one surfactant. In this embodiment, the surfactant is preferably a polymeric surfactant based on modified crosslinked copolymer of acrylic acid. Suitable surfactants are Pemulen Tr-1 and Pemulen Tr-2 (Lubrizol Corporation). While such surfactants are dissolved in the first and/or second discontinuous phase during preparation of the composition, the surfactant partitions between the discontinuous phase(s) and the continuous aqueous phase in the resulting composition.

Preferably, the composition disclosed herein has a total surfactant content of less than 5 wt % by weight of the composition, more preferably less than 2.5 wt %, still more preferably less than 2 wt %, still more preferably less than 1 wt %, and most preferably less than 0.5 wt %. Preferably, the total surfactant content is at least 0.1 wt %. As used herein, the term "total surfactant content" refers to the sum of the weight percentages of all of the surfactants present in the composition. As noted above, the surfactant(s) may be incorporated into one or more of the discontinuous phases and/or the continuous aqueous phase.

The use of low levels of surfactant is facilitated by the use of the first and second discontinuous phases described herein and minimises the skin irritancy caused by the composition. This is especially advantageous where the patient already has inflamed skin. The fact that such low levels of surfactant can be used is surprising because typically tacrolimus cream (non-ointment) formulations need very high levels of surfactant to act as a permeation enhancer or to allow the formation of a physically stable product.

Another advantage of using the preferred low levels of polar water-miscible liquids and/or surfactant is that the tacrolimus surprisingly has a higher chemical stability than in known formulations. Without wishing to be bound by theory, the present inventors believe that the polar water-miscible liquids and surfactants influence the partitioning of the tacrolimus between the oil and aqueous phases. Tacrolimus is oil-soluble. However, the presence of polar water-miscible liquids and surfactants increases the compatibility of the tacrolimus with the aqueous phase. The present inventors have found that this can lead to a significantly greater aqueous exposure of the tacrolimus, causing it to decompose. By contrast, in the present composition, the preferred low levels of polar water-miscible liquids and/or surfactant mean that there is less aqueous exposure of the tacrolimus and consequently higher chemical stability.

Preferably, the tacrolimus is chemically stable for at least 12 months at 5° C.±3° C., as measured at 60% RH±5%. The stability is measured after storage in a sealed amber glass jar. The jar is sealed in air. By "chemically stable" it is meant an HPLC assay of 100%±5% relative to the measurement at t=0.

Preferably, the tacrolimus is chemically stable for at least 12 months at 25° C.±2° C., as measured at 60% RH±5%. The stability is measured after storage in a sealed amber glass jar. The jar is sealed in air. Again, by "chemically stable" it is meant an HPLC assay of 100%±5% relative to the measurement at t=0.

Preferably, the tacrolimus is chemically stable for at least 6 months at 40° C.±3° C. The stability is measured after storage in a sealed amber glass jar. The jar is sealed in air. "Chemically stable" takes the same meaning as above.

Preferably, the composition comprises from 0.005 to 2 wt % tacrolimus by weight of the composition, more preferably from 0.01 to 1 wt %, still more preferably from 0.03 to 0.5 wt %, and most preferably about 0.1 wt %. Advantageously, the present invention allows comparable tacrolimus loading to the known ointment formulations while achieving improved aesthetics and patient compliance.

Preferably, the composition comprises from 5 to 40 wt % first discontinuous phase by weight of the composition, preferably from 10 to 30 wt %, more preferably from 10 to 25 wt %, still more preferably from 15 to 25 wt % and most preferably about 20 wt %.

Preferably, the composition comprises from 5 to 40 wt % second discontinuous phase by weight of the composition, preferably from 10 to 30 wt %, more preferably from 10 to 25 wt %, still more preferably from 15 to 25 wt % and most preferably about 20 wt %. Surprisingly, the permeation of the formulation is maximised when the amount of the second discontinuous phase is relatively low. This is demonstrated in an in vitro model in the Examples.

Preferably, the first oil is present in an amount of from 5 to 40 wt % by weight of the composition, more preferably from 10 to 30 wt %, still more preferably from 10 to 25 wt %, still more preferably from 15 to 25 wt % and most preferably about 20 wt %. Preferably, the second oil is present in an amount of from 5 to 40 wt % by weight of the composition, more preferably from 10 to 30 wt %, still more preferably from 10 to 25 wt %, still more preferably from 15 to 25 wt % and most preferably about 20 wt %. Preferably, the composition has a weight ratio of the second oil to the first oil of from 1:3 to 3:1, more preferably from 1:2 to 2:1, still more preferably from 2:3 to 3:2 and most preferably about 1:1. As is demonstrated in the Examples, the present inventors have found that the ratio of the second oil to the first oil should not be overly high if the permeation of the formulation is to be maximised. This is demonstrated in an in vitro model in the Examples.

Preferably, the composition comprises at least 10 wt % water by weight of the composition, preferably at least 20 wt %, more preferably at least 30 wt %, still more preferably at least 40 wt %, and most preferably at least 50 wt %. Preferably, the composition comprises at most 70 wt % water by weight of the composition. The excellent solubility of the tacrolimus in the first discontinuous phase means that relatively high water levels can be used, without causing excessive aqueous exposure of the active. Relatively high levels of water provide a less greasy feel to the skin, further improving patient compliance.

Preferably, the composition comprises at most two discontinuous phases. Preferably, the composition comprises no oils other than the first and second oils described herein.

Preferably, the composition further comprises at least one pharmaceutically acceptable excipient.

Preferably, the composition of the present invention has a mean droplet diameter (that is, a discontinuous phase droplet diameter) of from 1 to 30 μm, preferably from 1 to 20 μm. Such droplet diameters are to be contrasted with microemulsions, which typically have a mean droplet diameter of from 1 to 100 nm. In the context of the present invention, droplet diameter is measured by use of a Malvern Mastersizer 2000 laser diffraction particle size analyser.

The composition of the present invention may be in the form of a macroemulsion. Macroemulsions are known in the art and are distinct from microemulsions in that they have a larger mean droplet diameter. Moreover, unlike microemulsions, macroemulsions are thermodynamically unstable. As a result of this relative thermodynamic instability, macroemulsions are typically prepared in a different manner from microemulsions. For example, macroemulsion formation typically requires stirring/shear and usually, whereas microemulsions effectively form spontaneously.

Alternatively, the composition of the present invention may be in the form of a polyaphron dispersion. Polyaphron dispersions are known in the art and are disclosed in the following literature references by Sebba: "Biliquid Foams", J. Colloid and Interface Science, 40 (1972) 468-474 and "The Behaviour of Minute Oil Droplets Encapsulated in a Water Film", Colloid Polymer Sciences, 252 (1979) 392-396, Hicks "Investigating the Generation, Characterisation, and Structure of Biliquid Foams", PhD Thesis, University of Bristol, 2005, Crutchley "The Encapsulation of Oils and Oil Soluble Substances Within Polymer Films", PhD Thesis, The University of Leeds, 2006 and Lye and Stuckey, Colloid and Surfaces, 131 (1998) 119-136. Aphrons are also disclosed in U.S. Pat. No. 4,486,333 and WO 97/32559. Suitable methods of manufacturing polyaphron dispersions are described in WO 03/064024.

Preferably, the composition is in the form of a lotion or cream. Lotions and creams in the context of the present invention are to be distinguished from, for example, shaving foams, which have a much higher surfactant content in order to produce the desired foam in use. The present inventors have found that the use of two discontinuous phases as described herein enables the provision of a physically and chemically stable tacrolimus lotion or cream composition with good patient tolerability and perceived aesthetics, good efficacy and low irritancy.

Preferably the composition of the present invention is dispersible in water. Preferably the composition of the present invention is dilutable in water. This increases the flexibility of use of the invention, for example in improving the application of the composition to the scalp through hair by leaving the hair wet, or from rinsing the preparation from any topical surface should the desire or need arise, or by the easy removal by rinsing of product from accidental contamination of clothing. These advantages improve the in-use experience of users and improve patient compliance.

Preferably, the composition has a pH of from 3.5 to 6, more preferably from 4 to 5.5, still more preferably from 4.5 to 5.25, and most preferably from 4.5 to 5. The present inventors have found that controlling the pH of the composition to within these limits improves the stability of the tacrolimus and the composition as a whole. This is surprising because in the prior art it is conventional to use a lower pH (see, for example, US 2011/0201639 and US 8574562). It will be understood that any suitable acid or base may be used to adjust the pH to the appropriate value or pH range. Advantageously and preferably, the pH of the composition may be stabilised by the incorporation of a suitable buffer into the continuous aqueous phase. Suitable buffer systems having a pH within the specified range will be familiar to those skilled in the art.

Preferably, the composition is physically stable for at least 12 months at 5° C.±3° C., as measured at 60% RH±5%. The stability is measured after storage in a sealed amber glass jar. The jar is sealed in air. By "physically stable" it is meant that the composition appears as a homogeneous cream with no gross apparent rheological or appearance changes from t=0.

Preferably, the composition is physically stable for at least 12 months at 25° C.±2° C., as measured at 60% RH±5%. The stability is measured after storage in a sealed amber glass jar. The jar is sealed in air. Again, by "physically stable" it is meant that the composition appears as a homogeneous cream with no gross apparent rheological or appearance changes from t=0.

Preferably, the tacrolimus is physically stable for at least 6 months at 40° C.±3° C., as measured at 60% RH±5%. The stability is measured after storage in a sealed amber glass jar. The jar is sealed in air. "Physically stable" takes the same meaning as above.

Preferably, the composition of the present invention further comprises a gelling agent and/or a rheology modifying agent, such as a viscosity modifier. The gelling agent may, for example, be selected from alginate gums or their salts, guar gum, locust bean gum, xanthan gum, gum acacia, gelatin, hydroxymethylcellulose, hydroxyethylcellulose, hydroxypropylcellulose, carboxymethylcellulose or its salts, bentonites, magnesium aluminum silicates, "Carbomers" (salts of cross-linked polymers of acrylic acid), or glyceryl polymethacrylates or their dispersions in glycols. It will be understood that other suitable gelling agents may be used. Additionally, it has been found that some of the gelling agents (for example, carbomers) may also function as a chemical buffering agents thus preventing unwanted variation in the pH of the composition during storage and use. Where a viscosity modifier is used, this is preferably a polymeric cellulosic thickener. The inclusion of a gelling agent and/or rheology modifying agent provides additional stability against creaming and ensures that the active concentration is uniform throughout the composition. The use of these components is described in WO97/32559. The choice of gelling/thickening agents also allows for control of formulation viscosity from a thin lotion that is readily pourable to a thick cream with a significant resistance to flow.

Preferably, the composition of the present invention comprises from 0.05 to 5.0% by weight of a gelling agent, preferably from 0.1 to 2.0% by weight and more preferably from 0.2 to 1.0% by weight of the composition. In one embodiment of the present invention the composition has the consistency of a gel.

The compositions of the present invention may also contain other additives such as preservatives (for instance to prevent microbiological spoilage), buffering agents (for the control of pH and to avoid instability and damage to the skin's acid mantle) and antioxidants. Where a preservative is used, it is preferably present in an amount of from 0.5 to 1 wt %, more preferably from 0.6 to 0.8 wt %, by weight of the composition. The preservative is preferably selected from the group consisting of benzyl alcohol, phenoxyethanol, sodium benzoate, and combinations of two or more thereof. More preferably the preservative is phenoxyethanol. These additives may be included in the continuous or the discontinuous phase of the polyaphron dispersion. It will be understood that the inclusion of these additives will be at the levels and with the type of materials which are found to be effective and useful. Care needs to be taken in the choice and amount of these additives to prevent compromise to the other performance advantages of the present invention.

In an especially preferred embodiment, the composition of the present invention comprises a first discontinuous phase comprising diisopropyl adipate and tacrolimus;
a second discontinuous phase comprising mineral oil; and
a continuous aqueous phase;

preferably wherein the tacrolimus is substantially present in the first discontinuous phase;

wherein the composition comprises less than 1 wt % surfactant by weight of the composition;

wherein the composition comprises less than 5 wt % by weight of the composition of $C_1$-$C_4$ alcohols, polyethylene glycol, ethylene glycol, propylene glycol, butylene glycol, pentylene glycol, glycerol, diethylene glycol mono ethyl ether, propylene carbonate and mixtures of two or more thereof; and wherein the composition is in the form of a lotion or cream.

In a further especially preferred embodiment, the composition of the present invention comprises a first discontinuous phase comprising diisopropyl adipate and tacrolimus;

a second discontinuous phase comprising mineral oil; and a continuous aqueous phase;

preferably wherein the tacrolimus is substantially present in the first discontinuous phase;

wherein the composition comprises less than 1 wt % surfactant by weight of the composition;

wherein the composition comprises less than 1 wt % by weight of the composition of $C_1$-$C_4$ alcohols, polyethylene glycol, ethylene glycol, propylene glycol, butylene glycol, pentylene glycol, glycerol, diethylene glycol mono ethyl ether, propylene carbonate and mixtures of two or more thereof; and wherein the composition is in the form of a lotion or cream.

According to a second aspect, there is provided a composition as described herein for use in the treatment of psoriasis or atopic dermatitis.

According to a third aspect, there is provided a composition as described herein for use in the manufacture of a medicament for the treatment of psoriasis or atopic dermatitis.

According to a fourth aspect, there is provided a composition as described herein for use in a method of treatment of the human or animal body by therapy.

According to a fifth aspect, there is provided a method of treating psoriasis or atopic dermatitis in a human or animal patient comprising administering to a patient in need thereof an effective amount of a composition as described herein.

The composition as described herein may be applied to the scalp or other skin surface through hair. Preferably in this embodiment the hair is wetted (for example by use of water with or without shampoo, and then towel dried). The product may then be applied to the scalp in a suitable amount and then massaged into the scalp through the hair. The hair may then be left to dry naturally or dried using a hair dryer. Advantageously, the water-dispersible form of the formulation enables an even distribution of the actives on the skin using this process. Alternatively, or additionally, the composition may be massaged into the scalp through dry hair and left for a suitable period (which may be 8 to 12 hours) after which the excess or reminder may be rinsed out with water with or without shampoo. Preferably the composition is applied to a human or animal in unit dosage form.

According to a sixth aspect, the present invention provides a package comprising the composition disclosed herein. Preferably, the package is a tube or an airless pump. For example, a tube can be squeezed for topical application of the composition.

According to a seventh aspect, the present invention provides a method of manufacturing a composition for topical application, the method comprising:

(i) providing a first oil comprising tacrolimus;
(ii) providing a second oil;
(iii) providing an aqueous component; and
(iv) dispersing the first oil and the second oil in the aqueous component to form a composition for topical application comprising a first discontinuous phase comprising a first oil and tacrolimus, a second discontinuous phase comprising a second oil, and a continuous aqueous phase;

wherein the first oil is different from the second oil.

Preferably, the composition produced by the method is the composition as described above. Methods for preparing such oil-in-water dispersions are known in the art, for example in G. Godwin, Harry's Cosmeticology 7$^{th}$ Edition, 1982. It will be understood by those skilled in the art that other manufacturing methods may be used, as appropriate.

As noted above, the composition may be a polyaphron dispersion. Suitable methods for preparing polyaphron dispersions are described in U.S. Pat. No. 4,486,333. It will be understood by those skilled in the art that other manufacturing methods may be used, as appropriate.

Preferably, the method further comprises packaging the composition.

The foregoing aspects may be freely combined with any of the foregoing aspects disclosed herein.

The present invention will now be described in relation to the following non-limiting figures:

FIG. 1 is a simple schematic diagram depicting the structure of a composition in accordance with the present invention. The lighter circles represent the first discontinuous phase (comprising a first oil and tacrolimus), the darker circles represent the second discontinuous phase (comprising a second oil), and the background represents the continuous aqueous phase.

Figure 2:
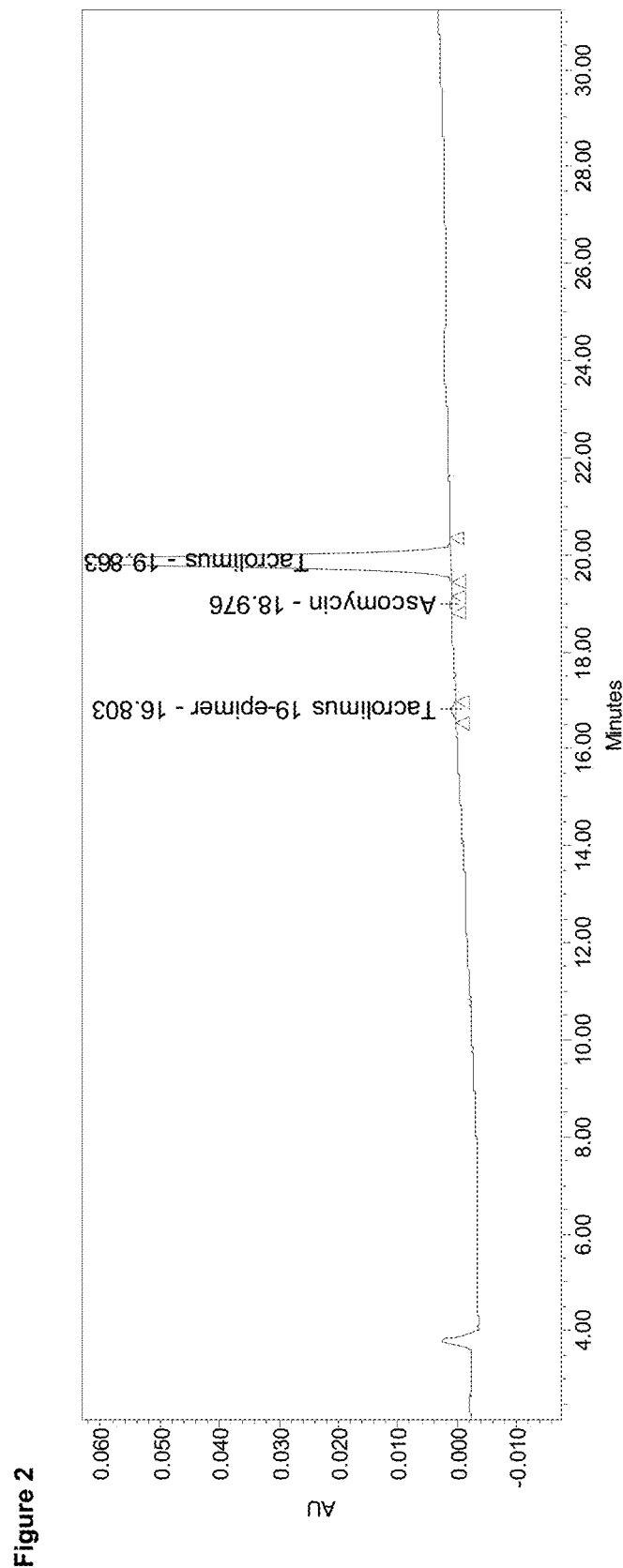

FIG. 2 is a HPLC chromatogram of a tacrolimus standard at t=0, used in Example 1. Peaks for tacrolimus (19.863 minutes), tacrolimus 19-epimer (16.803 minutes) and ascomycin (18.976 minutes) are observed. HPLC conditions are: Column: Luna C18(2), 3 μm particle size, 4.6×150 mm column (Waters), Flow rate: 1.5 mL/minute. Column Temperature: 25° C.

Figure 3:
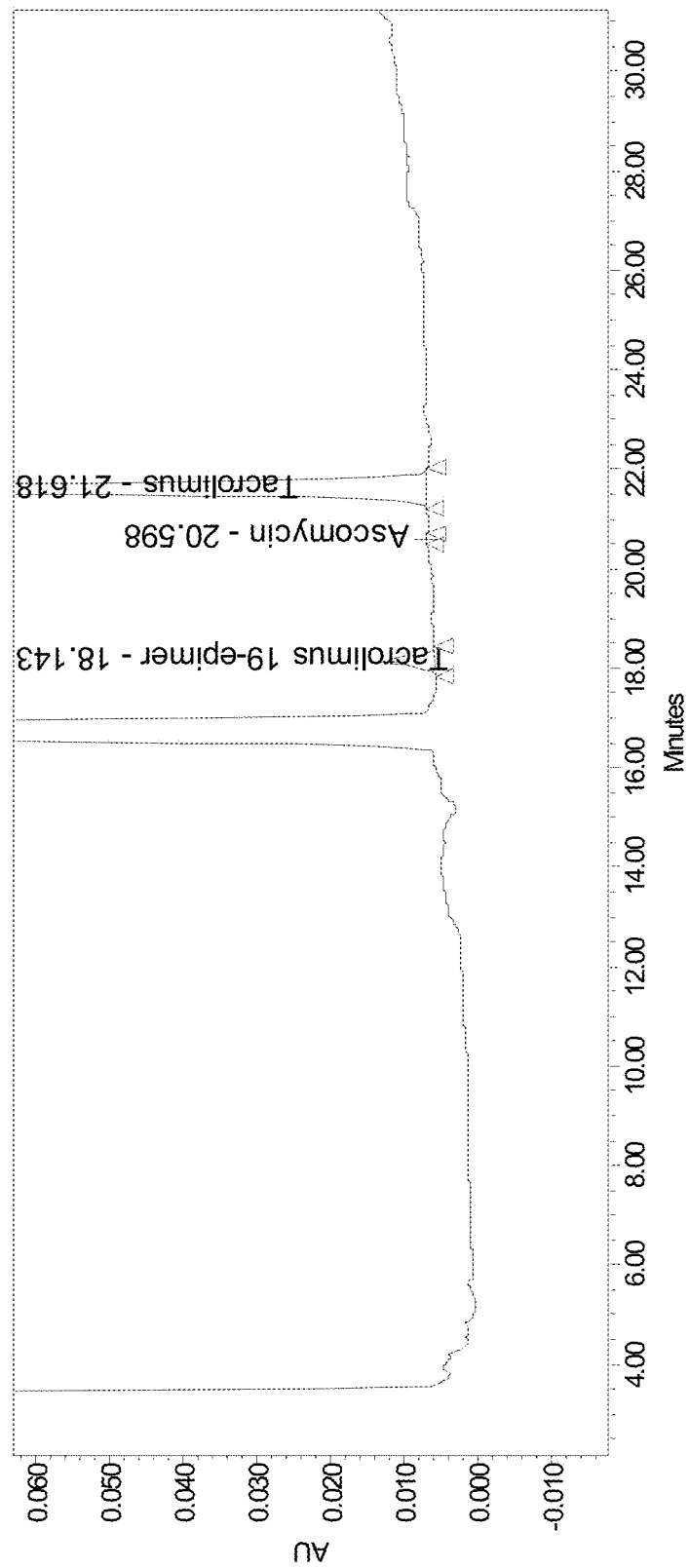

FIG. 3 is a HPLC chromatogram of Sample 1 of Example 1 at t=0. HPLC conditions are: Column: Luna C18(2), 3 μm particle size, 4.6×150 mm column (Waters), Flow rate: 1.5 mL/minute. Column Temperature: 25° C.

Figure 4:
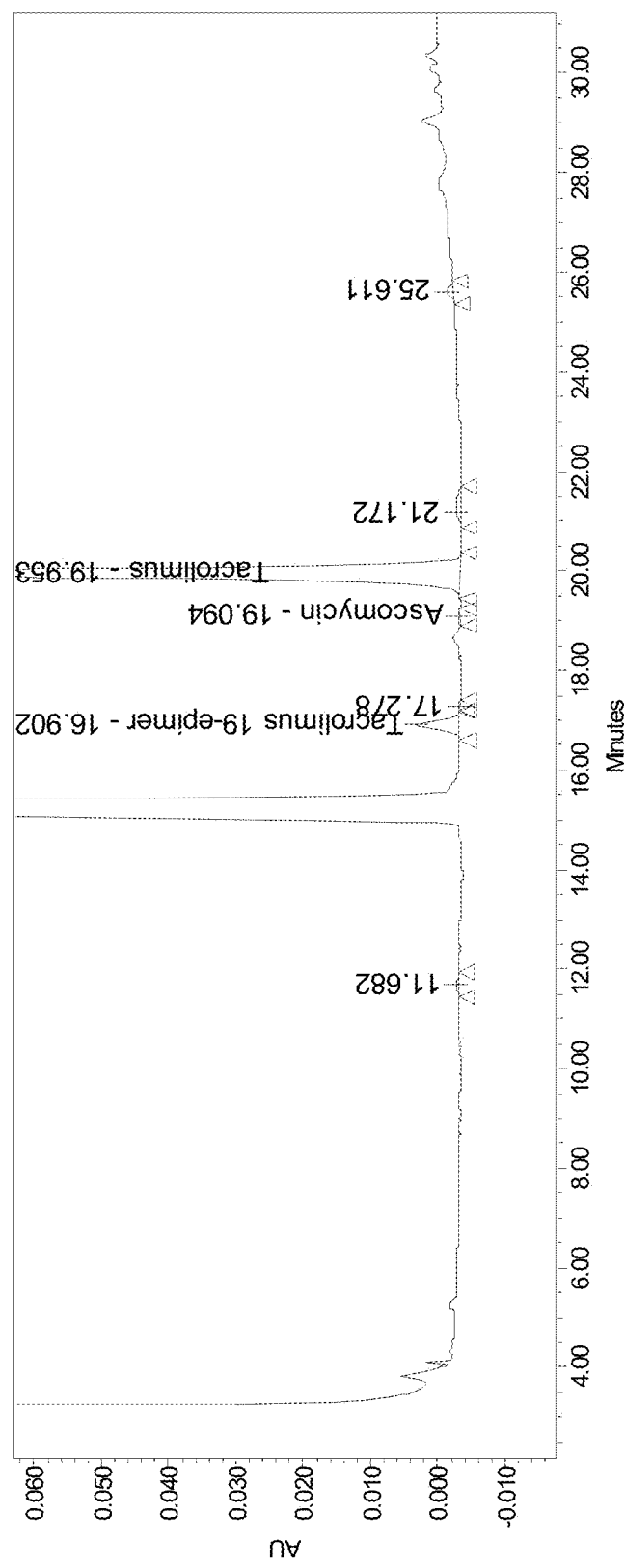

FIG. 4 is a HPLC chromatogram of Sample 1 of Example 1 at t=6 months at 40° C. HPLC conditions are: Column: Luna C18(2), 3 μm particle size, 4.6×150 mm column (Waters), Flow rate: 1.5 mL/minute. Column Temperature: 25° C.

Figure 5:
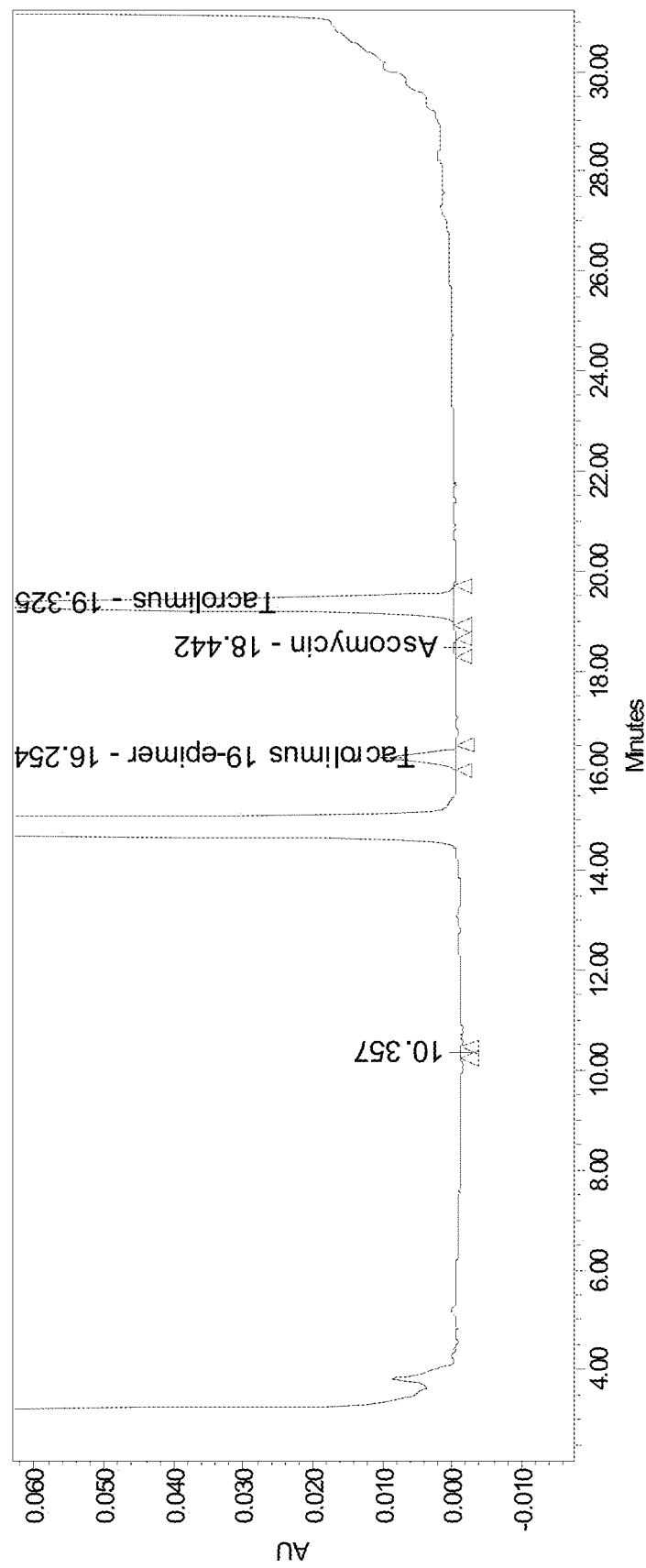

FIG. 5 is a HPLC chromatogram of Sample 9 of Example 1 at t=0. HPLC conditions are: Column: Luna C18(2), 3 μm particle size, 4.6×150 mm column (Waters), Flow rate: 1.5 mL/minute. Column Temperature: 25° C.

Figure 6:
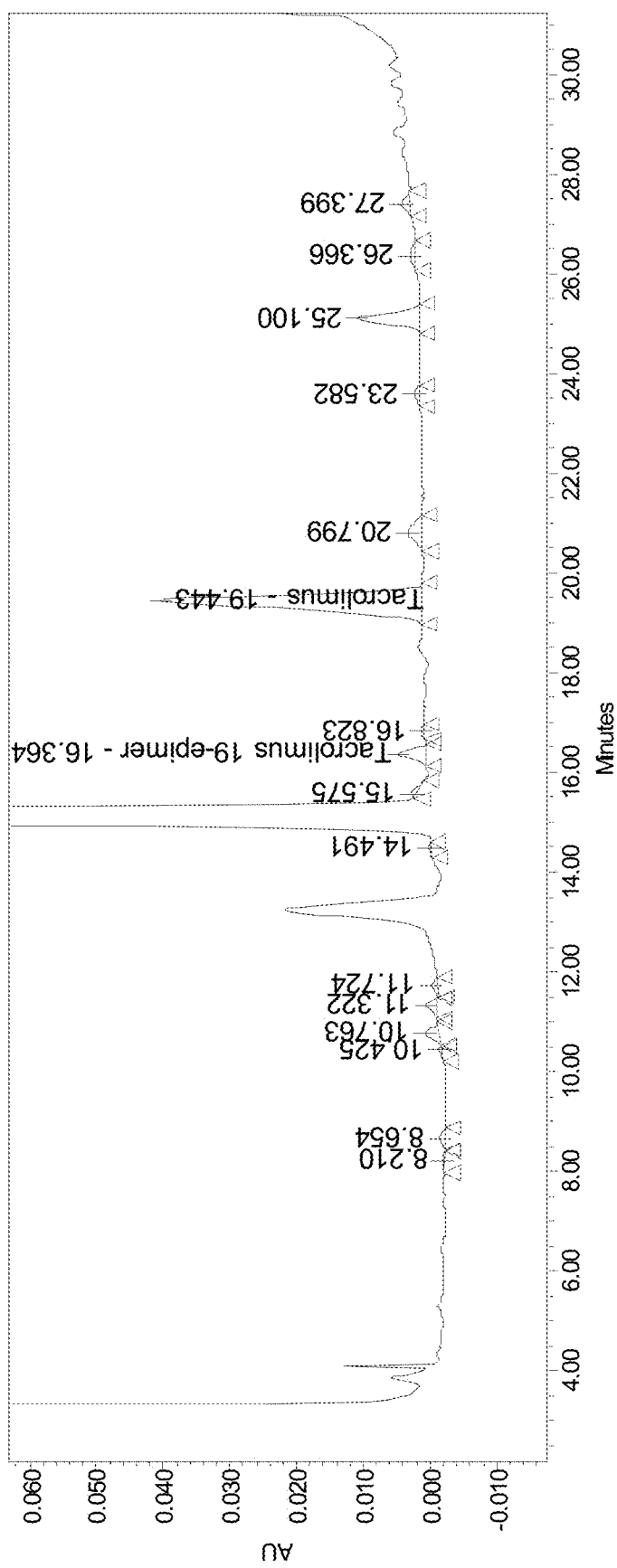

FIG. 6 is a HPLC chromatogram of Sample 9 of Example 1 at t=6 months at 40° C. HPLC conditions are: Column: Luna C18(2), 3 μm particle size, 4.6×150 mm column (Waters), Flow rate: 1.5 mL/minute. Column Temperature: 25° C.

Figure 7:
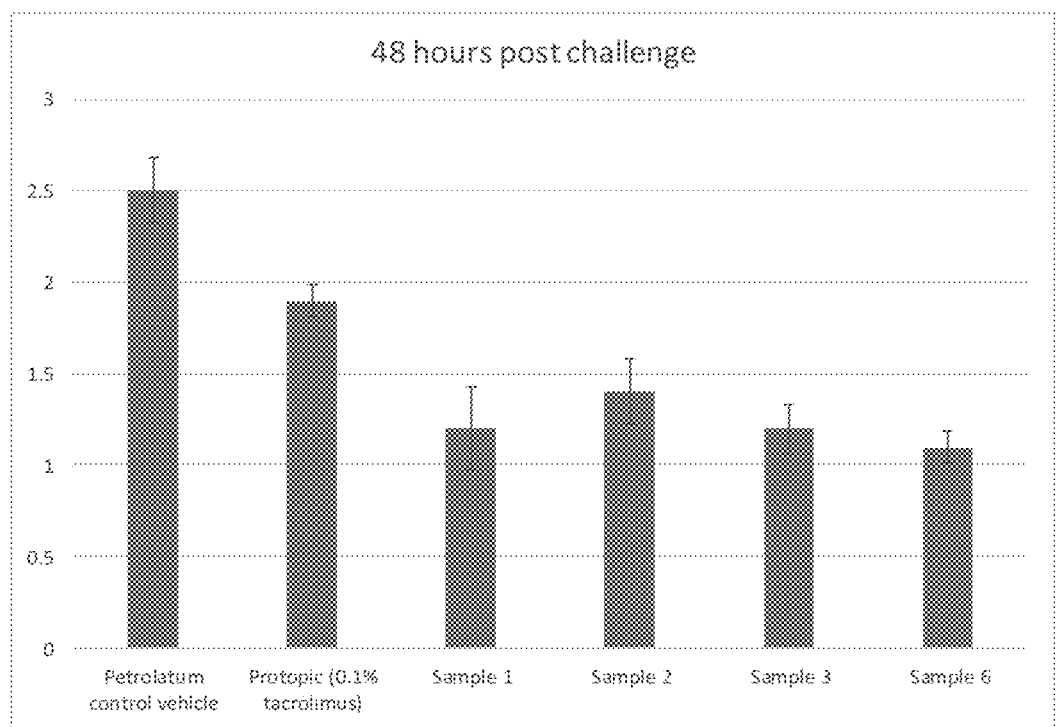

FIG. 7 is a bar chart showing the effect of the compositions of Samples 1, 2, 3 and 6 on erythema score 48 hours after an initial application of the compositions. The error bars indicate standard error of the mean.

Figure 8:
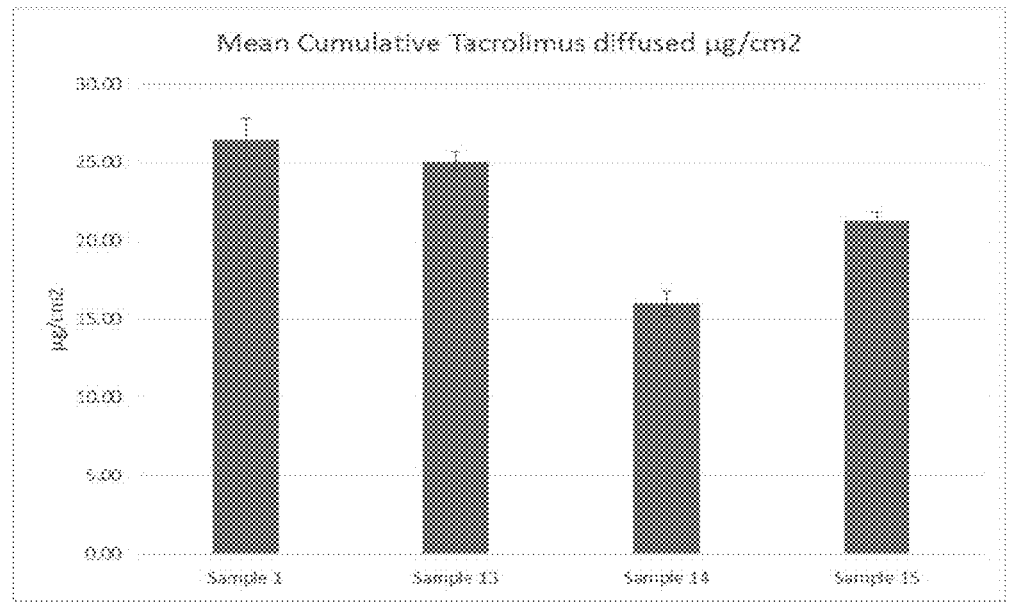

FIG. 8 is a bar chart showing the in vitro diffusion of Samples 1, 13, 14 and 15 in μg/cm$^2$. The y-axis indicates mean cumulative tacrolimus diffused in μg/cm$^2$. The error bars indicate standard deviation.

Figure 9:
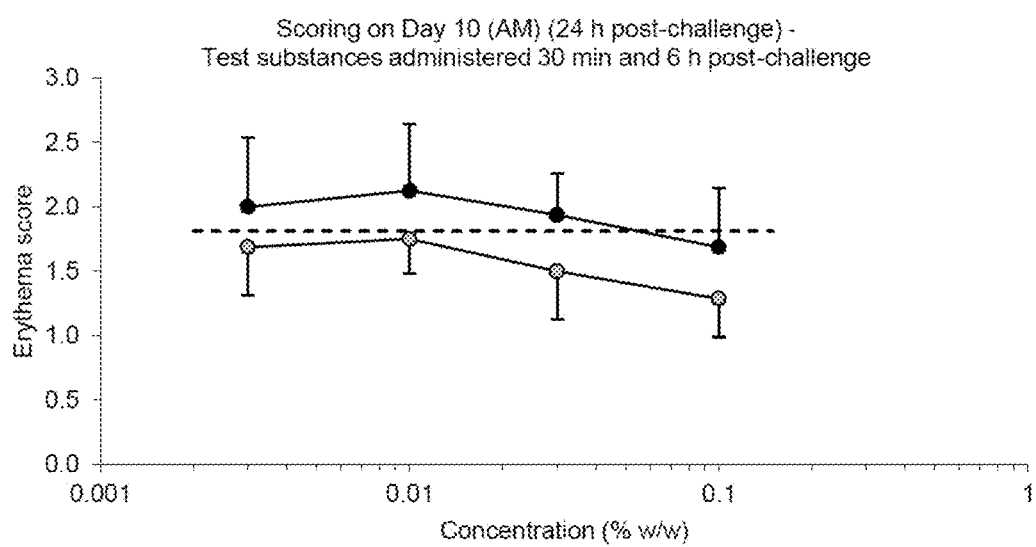

FIG. 9 is a dose response graph of Samples 1, 22, 23 and 24 (at tacrolimus concentrations of 0.1%, 0.03%, 0.01% and 0.003% respectively) compared to corresponding variants of tacrolimus ointment in Landrace Swine model of allergic contact dermatitis. Black circles: Tacrolimus ointment variants; Grey circles: Sample 1 tacrolimus variants; Dotted line: Sample 21 (control vehicle). The x-axis represents tacrolimus concentration, and the y-axis represents the Erythema score on day 10 (24 h post-challenge). The error bars indicate standard deviation.

The present invention will now be described in relation to the following non-limiting examples.

EXAMPLE 1

The following compositions were prepared and the tacrolimus stability measured both in an initial assay and after 6 months at 40° C.:

| | Component | Sample 1 | Sample 2 | Sample 3 | Sample 4 | Sample 5 | Sample 6 | Sample 7 | Sample 8 | Sample 9 | Sample 10 |
|---|---|---|---|---|---|---|---|---|---|---|---|
| Tacrolimus | 3 | 0.10 | 0.10 | 0.10 | 0.10 | 0.10 | 0.10 | 0.10 | 0.10 | 0.10 | 0.10 |
| Mineral Oil | 2 | 20.00 | 20.00 | 20.00 | 20.00 | 20.00 | 20.00 | 20.00 | 20.00 | 20.00 | 20.00 |
| Propylene glycol | 1&4* | — | 20.00 | — | 30.00 | — | 10.00 | — | — | — | — |
| Transcutol P ™ | 1&4* | — | — | 20.00 | — | — | 10.00 | — | — | — | — |
| Hexylene glycol | 1&4* | — | — | — | — | 12.00 | — | — | — | — | — |
| Pentylene glycol | 1&4* | — | — | — | — | — | — | — | — | 20.00 | — |
| Capric/caprylic triglycerides - Miglyol 812 ™ | 3 | 10.00 | 10.00 | 10.00 | 10.00 | 10.00 | 10.00 | 10.00 | 10.00 | 10.00 | 10.00 |
| Diisopropyl adipate | 3 | 5.00 | 5.00 | 5.00 | 5.00 | 5.00 | 5.00 | — | — | 5.00 | 5.00 |
| Diethyl sebacate | 3 | — | — | — | — | — | — | 5.00 | — | — | — |
| Dibutyl adipate | 3 | — | — | — | — | — | — | — | 5.00 | — | — |
| Isopropyl myristate | 3 | 5.00 | 5.00 | 5.00 | 5.00 | 5.00 | 5.00 | 5.00 | 5.00 | 5.00 | 5.00 |
| Carbomer - Ultrez 10 ™ | 4 | 1.00 | 1.00 | 1.00 | 1.00 | 1.00 | 1.00 | 1.00 | 1.00 | 1.00 | 1.00 |
| Phenoxyethanol | 4 | 0.70 | 0.70 | 0.70 | 0.70 | 0.70 | 0.70 | 0.70 | 0.70 | 0.70 | 0.70 |
| Laureth 4 | 2&3* | 0.40 | 0.40 | 0.40 | 0.40 | 0.40 | 0.40 | 0.40 | 0.40 | 0.40 | 9.40 |
| Hydroxyethyl cellulose - Natrosol 250L ™ | 4 | 0.20 | 0.20 | 0.20 | 0.20 | 0.20 | 0.20 | 0.20 | 0.20 | 0.20 | 0.20 |
| Sodium citrate | 4 | 0.164 | 0.164 | 0.164 | 0.164 | 0.164 | 0.164 | 0.164 | 0.164 | 0.164 | 0.164 |
| Butylated hydroxytoluene | 3 | 0.10 | 0.10 | 0.10 | 0.10 | 0.10 | 0.10 | 0.10 | 0.10 | 0.10 | 0.10 |
| Citric acid | 4 | 0.095 | 0.095 | 0.095 | 0.095 | 0.095 | 0.095 | 0.095 | 0.095 | 0.095 | 0.095 |
| Polysorbate 20 | 1 | 0.04 | 0.04 | 0.04 | 0.04 | 0.04 | 0.04 | 0.04 | 0.04 | 0.04 | 0.04 |
| Sodium hydroxide (20% aqueous solution) | 5 | q.s. | q.s. | q.s. | q.s. | q.s. | q.s. | q.s. | q.s. | q.s. | q.s. |
| Water | 1 and 4 (5 if required) | q.s. | q.s. | q.s. | q.s. | q.s. | q.s. | q.s. | q.s. | q.s. | q.s. |
| Total | | 100.00 | 100.00 | 100.00 | 100.00 | 100.00 | 100.00 | 100.00 | 100.00 | 100.00 | 100.00 |
| Initial assay | | 103.6 | 102.4 | 102.7 | 103.9 | 103.2 | 100.4 | 101.0 | 99.7 | 98.2 | 97.8 |
| 6 months @40° C. assay | | 101.3 | 90.9 | 83.9 | 79.7 | 89.6 | 83.7 | 91.6 | 93.1 | 55.5 | 88.2 |

Key to components:
1 Dispersion aqueous phase
2 API Non-solvent oil phase
3 API solvent oil phase
4 Gel/thickener
5 pH/water adjustment
*The substance is split in proportion between the two phases depending on the relative size of the phases. For example, if the two oil phases are of the same mass, an equal mass of surfactant is added to each oil phase. If the first oil phase has twice the mass of the second oil phase, the surfactant is split in a 2:1 ratio by mass between the two phases.

The components are made separately before being sequentially added whilst undergoing suitable stirring. Components 1-3 in combination formed 50 wt % of the final formula in each case, component 4 formed 48 wt % and component 5 formed 2 wt %.

Each sample was stored in a closed, airtight glass container with headspace comprising no more than 5% by volume of the total usable volume of the container. Each container containing a sample was stored at a constant temperature of 40° C. in a standard laboratory incubator (for example, Memmert IF260PLUS Incubator). The storage period for each sample was six months, following which the chemical stability was measured.

A stability of 100±5% assay indicates that the tacrolimus was chemically stable for six months at 40° C. A stability of 100±2% assay indicates that the chemical stability of the tacrolimus was particularly high.

The chemical stability of the tacrolimus in each sample after the storage period was measured by a HPLC method. The HPLC method was as follows:

| | |
|---|---|
| HPLC System | Waters Photodiode Array Detector |
| | Waters Separation Module |
| | Waters Empower2 or Empower3 Data Processing Software |
| Column | Luna C18(2), 150 × 4.6 mm, 3 µm |
| Guard Column | SecurityGuard C18 4 × 3.0 mm |
| Detection | 220 nm |
| Sample Temperature | 5° C. |
| Column Temperature | 60° C. |
| Flow Rate | 1.5 mL/min |
| Mobile Phase | Mobile Phase A: Solution A: Solution B (80:20) |
| | Mobile Phase B: Solution A: Solution B (20:80) |
| Injection Volume | 50 µL |
| Run Time | 50 min |

| Time (min) | Tacrolimus | |
|---|---|---|
| | % A | % B |
| 0 | 85 | 15 |
| 25 | 42 | 58 |

-continued

| | | |
|---|---|---|
| 35 | 0 | 100 |
| 40 | 0 | 100 |
| 40.1 | 85 | 15 |
| 50 | 85 | 15 |

Mobile Phase Preparation

Solution A: Prepare a solution of 6 mM orthophosphoric acid in water by adding 0.4 mL into 1000 mL purified water (typically prepare 3 L).

Solution B: Prepare a mixture of acetonitrile and tert-butyl methyl ether in the ratio 81:19%, respectively (typically prepare 3 L).

Mobile phases A and B are prepared as a mixture of solutions A and B in the ratios detailed in the table above.

Sample Preparation

Acetonitrile is used as the sample diluent.
Prepare solutions in amber glassware.

Procedure

1. Accurately weigh approximately 1.0 g of sample into a 10 ml volumetric flask, minimizing sample on the neck of the flask.
2. Add approximately 5 mL sample diluent to the volumetric flask and vortex mix for 2 minutes.
3. Allow to equilibrate to room temperature and then make the volumetric flask to volume with sample diluent. Thoroughly mix by stirring for 1 hour
4. Transfer an aliquot of the solution to a 2 ml centrifuge tube and centrifuge for 10 minutes at 13,000 rpm.
5. Filter through a 0.45 µm PTFE syringe filter Standard Preparation A solution of tacrolimus in acetonitrile was prepared at a concentration of 100 µg/mL.

The HPLC chromatogram for the tacrolimus standard using this method is shown in FIG. 2. The HPLC chromatograms for Sample 1 are shown in FIG. 3 (t=0) and FIG. 4 (t=6 months at 40° C.). The HPLC chromatograms for Sample 9 are shown in FIG. 5 (t=0) and FIG. 6 (t=6 months at 40° C.).

Approximate Retention Times

| | |
|---|---|
| Tacrolimus 19-epimer | 16.1 minutes |
| Ascomycin | 18.3 minutes |
| Tacrolimus | 19.1 minutes |
| Tacrolimus 8-propyl analogue | 20.9 minutes |

Discussion of Stability Results

As can be seen from the stability data, Sample 1 (which uses diisopropyl adipate, isopropyl myristate and caprylic capric triglycerides for the first discontinuous phase and does not contain polar water-miscible liquids) is the most stable formulation in terms of tacrolimus stability.

In Sample 2, 3, 4, 5 and 9 the tacrolimus was less stable. These formulations contain various polar water-miscible liquids (propylene glycol, Transcutol P™, hexylene glycol or pentylene glycol) at 12-30 wt %. This lower stability is thought to be due to the polar non-aqueous solvents influencing the partitioning of the tacrolimus between the oil and aqueous phases. In particular, it is thought that the aqueous exposure of the tacrolimus is greater in Sample 2, 3, 4, 5 and 9 than in Example 1, leading to increased degradation of the tacrolimus. The enhanced chemical stability of Sample 1 relative to Sample 9 can be seen in FIGS. 3-6.

Sample 10 is the same as Sample 1 except that it has an increased level of the surfactant Laureth 4 (9.4 wt %). The measured tacrolimus stability was significantly lower than in Sample 1. Again, this is thought be due to the surfactant influencing the portioning of the tacrolimus between the oil and aqueous phases. In particular, it is thought that the aqueous exposure of the tacrolimus is greater in Sample 10 than in Sample 1, leading to increased degradation of the tacrolimus.

A comparison of Samples 1, 7 and 8 shows that the use of diisopropyl adipate in the first discontinuous phase (Example 1) gives rise to greater tacrolimus stability than using diethyl sebacate or dibutyl adipate in the first discontinuous phase (Sample 7 and 8 respectively). This is surprising because all three oils have a similar solubility profile for tacrolimus (see discussion in Example 2).

All samples were observed to be physically stable after 6 months at 40° C., i.e. each sample appeared as a homogeneous cream with no gross apparent rheological or appearance changes from t=0.

EXAMPLE 2

In this Example, the solubility of tacrolimus in various oil solvents was measured by HPLC.

Approximately 40 mg of tacrolimus was weighed and a known quantity (1-2 g) of oil was added and stirred for 5 hours at room temperature. If by visual examination the tacrolimus had failed to dissolve further oil was added up to a maximum of 10 g. If the tacrolimus appeared to be fully dissolved in under 10 g of oil the sample was then placed at 4° C. overnight. If the tacrolimus precipitated out after cold storage further oil was added and the above steps were repeated until dissolved or the 10 g of oil had been added. All samples were then centrifuged to ensure any non-dissolved tacrolimus was removed and the supernatant analysed by HPLC as described in Example 1. The refrigeration of the oil solvents provides confidence that the tacrolimus will remain in solution should the final formula be subjected to refrigeration or exposed to cold temperatures. It would not be unreasonable for a commercial product to experience such conditions. It is important that the tacrolimus does not precipitate out of solution. Such precipitation may cause the product to become physically or chemically unstable, or the tacrolimus to be non-homogeneously distributed.

Results

The solubility data for tacrolimus in oil solvents, as measured in accordance with the above method, is as follows:

| Solvent | Solubility (% wt) |
|---|---|
| Diethyl sebacate | 3.26* |
| Dibutyl adipate | 3.24* |
| Diisopropyl adipate | 3.08* |

-continued

| Solvent | Solubility (% wt) |
|---|---|
| Castor oil | 1.44 |
| Capric caprylic trigylcerides | 0.44 |
| Isopropyl palmitate | 0.26 |
| Isopropyl myristate | 0.25 |
| Isopropyl isostearate | 0.19 |
| Heptylmethylnonane | 0.006 |
| Cyclomethicone | 0.004 |
| Dimethicone | 0.004 |
| Mineral oil | 0.003 |

*HPLC assay within 95% of theoretical experiment maximum. Likely maximum solubility is greater than stated.

Based on the above data, the oils can be divided into three classes: good solvents (>1% solvency), moderate (0.15-1% solvency) and effectively non-solvents (<0.1%).

Given that tacrolimus has similar solubility in diethyl sebacate, diisopropyl adipate and dibutyl adipate, it is surprising that diisopropyl adipate is significantly more effective at stabilising the tacrolimus than diethyl sebacate or dibutyl adipate (see Example 1).

Without wishing to be bound by theory, it is thought that the two ester linkages present in all three oils are protected more in diisopropyl adipate by steric hindrance caused by proximity/conformation of the methyl groups close to the bond. It is thought that degradation of this bond may subsequently impact the stability of the active, thus explaining the increased stability of Example 1.

EXAMPLE 3

An in vivo experiment using an allergic contact dermatitis model in Landrace swine (five pigs) compared Protopic™ (0.1% tacrolimus), a petrolatum control, and Samples 1-3 and 6.

The method involved administering Dinitrofluorobenzene (DNFB) and Dinitrochlorobenzene (DNCB) to skin patches to induce contact hypersensitivity, followed by treatment with one of Protopic™ (0.1% tacrolimus), a petrolatum control, and Samples 1-3 and 6.

The method is based on the protocol described in Mollison et al. J Invest Dermatol. 1999 May; 112(5):729-38: a macrolactam inhibitor of T helper type 1 and T helper type 2 cytokine biosynthesis for topical treatment of inflammatory skin diseases.

Method

Day 0: Application of 100 µl of 10% Dinitrofluorobenzene (DNFB) in acetone/DMSO/olive oil (45/5/50 v/v/v) to each of the outer aspects of both entire ears and bilateral sites on the lower abdomen≈20 cm².

Day 3: Application of 100 µl of 5% Dinitrofluorobenzene (DNFB) in acetone/DMSO/olive oil (45/5/50 v/v/v) to the internal pinnae of both ears patches and to bilateral sites on the lower thorax≈20 cm².

Day 9: Application of 61 µl of 0.6% Dinitrochlorobenzene (DNCB) in acetone/olive oil (95/5 v/v) to 18 rectangular test areas—9 on each side of the pig (3.5×3.5 cm, 12.25 cm²).

Day 9+30 minutes: Application of 61 µl of test formulations to test areas (3.5×3.5 cm, 12.25 cm²).

Scoring/assessment and then reapplication of test formulations was undertaken after 24 and 30 hours after the initial application of the test formulation. A further scoring was undertaken after 48 hours.

The patches were scored as follows:
0—no erythema
0.5—questionable erythema
1—faint or scattered erythema
2—moderate erythema without induration
3—strong erythema with focal areas of edema or induration
4—extreme erythema with uniform induration or edema Results

| | 24 hours | 30 hours | 48 hours | 48 hours standard deviation | 48 hours standard error |
|---|---|---|---|---|---|
| Petrolatum control vehicle | 3.1 | 3.1 | 2.5 | 0.4 | 0.18 |
| Protopic (0.1% tacrolimus) | 2.3 | 2.2 | 1.9 | 0.2 | 0.09 |
| Sample 1 | 1.5 | 1.4 | 1.2 | 0.5 | 0.22 |
| Sample 2 | 1.7 | 1.6 | 1.4 | 0.4 | 0.18 |
| Sample 3 | 1.4 | 1.4 | 1.2 | 0.3 | 0.13 |
| Sample 6 | 1.5 | 1.3 | 1.1 | 0.2 | 0.09 |

Pigs that rated a 3 or more at the 24 hr scoring for the petrolatum control were used for comparative purposes. Pigs that did not react strongly to the sensitisation would not allow sufficient differentiation in determining the efficacy of the active formulas.

The results at 48 hours are also shown in FIG. 7 (error bars indicate standard error of the mean). As is evident from FIG. 7 and the table above, the erythema score at 48 hours is similar for Samples 1-3 and 6. These erythema scores are significantly lower than for the Petrolatum control vehicle and Protopic™. Thus, the formulations of the present invention have higher in vivo efficacy than existing ointment formulations such as Protopic™.

EXAMPLE 4

Additional compositions were prepared using different surfactant systems. For comparison, the composition of Sample 1 is included in the table.

| | Component | Sample 1 | Sample 11 | Sample 12 |
|---|---|---|---|---|
| Tacrolimus | 3 | 0.10 | 0.10 | 0.10 |
| Mineral Oil | 2 | 20.00 | 20.00 | 20.00 |
| Capric/caprylic triglycerides - Miglyol 812 ™ | 3 | 10.00 | 10.00 | 10.00 |
| Diisopropyl adipate | 3 | 5.00 | 5.00 | 5.00 |
| Isopropyl myristate | 3 | 5.00 | 5.00 | 5.00 |
| Carbomer - Ultrez 10 ™ | 4 | 1.00 | 0.20 | 0.20 |
| Laureth 4 | 2&3* | 0.40 | — | 0.40 |
| Pemulen TR2 | 2&3* | — | 0.60 | — |
| Span 20 | 2&3* | — | — | 1.00 |
| PEG-20 cetyl ether | 2&3* | — | — | 1.00 |
| Phenoxyethanol | 4 | 0.70 | 0.70 | 0.70 |
| Hydroxyethyl cellulose - Natrosol 250L ™ | 4 | 0.20 | 0.20 | 0.20 |
| Sodium citrate | 4 | 0.164 | 0.164 | 0.164 |
| Butylated hydroxytoluene | 3 | 0.10 | 0.10 | 0.10 |
| Citric acid | 4 | 0.095 | 0.095 | 0.095 |
| Polysorbate 20 | 1 | 0.04 | — | 0.04 |

-continued

| Component | | Sample 1 | Sample 11 | Sample 12 |
|---|---|---|---|---|
| Sodium hydroxide (20% aqueous solution) | 5 | q.s. | q.s. | q.s. |
| Water | 1 and 4 (5 if required) | q.s. | q.s. | q.s. |
| Total | | 100.00 | 100.00 | 100.00 |
| Initial assay | | 103.6 | 104.5 | 102.7 |
| 6 months @ 40° C. assay | | 101.3 | — | — |

*The substance is split in proportion between the two phases depending on the relative size of the phases. For example, if the two oil phases are of the same mass, an equal mass of surfactant is added to each oil phase. If the first oil phase has twice the mass of the second oil phase, the surfactant is split in a 2:1 ratio by mass between the two phases.

The numbering and proportion of the components (1-5) is the same is in Example 1.

For both Examples 11 & 12 components were heated to 70° C. before combining. In the case of Example 12, a high shear rotostator (Silverson) device was used at 7000 rpm.

EXAMPLE 5

Compositions were prepared in which the second oil and its amount were varied. For comparison, the composition of Sample 1 is included in the table.

| Component | | Sample 1 | Sample 13 | Sample 14 | Sample 15 |
|---|---|---|---|---|---|
| Tacrolimus | 3 | 0.10 | 0.10 | 0.10 | 0.10 |
| Mineral Oil | 2 | 20.00 | — | 32.00 | — |
| Dimethicone 350 cst | 2 | — | 20.00 | — | — |
| Capric/caprylic triglycerides - Miglyol 812 ™ | 3 | 10.00 | 10.00 | 10.00 | 10.00 |
| Diisopropyl adipate | 3 | 5.00 | 5.00 | 5.00 | 5.00 |
| Isopropyl myristate | 3 | 5.00 | 5.00 | 5.00 | 5.00 |
| Carbomer - Ultrez 10 ™ | 4 | 1.00 | 1.00 | 1.00 | 1.00 |
| Laureth 4 | 2&3* | 0.40 | 0.40 | 0.52 | 0.20 |
| Phenoxyethanol | 4 | 0.70 | 0.70 | 0.70 | 0.70 |
| Hydroxyethyl cellulose - Natrosol 250L ™ | 4 | 0.20 | 0.20 | 0.20 | 0.20 |
| Sodium citrate | 4 | 0.164 | 0.164 | 0.164 | 0.164 |
| Butylated hydroxytoluene | 3 | 0.10 | 0.10 | 0.10 | 0.10 |
| Citric acid | 4 | 0.095 | 0.095 | 0.095 | 0.095 |
| Polysorbate 20 | 1 | 0.04 | 0.04 | 0.05 | 0.02 |
| Sodium hydroxide (20% aqueous solution) | 5 | q.s. | q.s. | q.s. | q.s. |
| Water | 1 and 4 (5 if required) | q.s. | q.s. | q.s. | q.s. |
| Total | | 100.00 | 100.00 | 100.00 | 100.00 |

*The substance is split in proportion between the two phases depending on the relative size of the phases. For example, if the two oil phases are of the same mass, an equal mass of surfactant is added to each oil phase. If the first oil phase has twice the mass of the second oil phase, the surfactant is split in a 2:1 ratio by mass between the two phases.

Sample 13: Mineral oil replaced with dimethicone
Sample 14: Extra mineral oil
Sample 15: No second discontinuous phase (comparative)

The formulations were tested in a Franz cell in vitro diffusion experiment though an artificial membrane. The membrane used was a Strat-M Membrane from Merck Millipore and is described as a synthetic, non-animal based model for transdermal diffusion testing that is predictive of diffusion in human skin. A phosphate buffered saline solution with 5% Bovine serum albumin and 5% isopropyl alcohol was used as the receptor phase. Cells with a surface area of 0.64 cm$^2$ and a receptor volume of approximately 2 cm$^3$ were used. Approximately 40 mg of formulation was applied at time 0, 24 and 48 hours and the cells were stirred and incubated at 37° C. throughout. The receptor phase was sampled and replaced at 24, 48 and 72 hours. Tacrolimus concentration was determined by HPLC in accordance with the above method and adjusted for individual cell receptor volume. Mean cumulative tacrolimus per cm$^2$ of membrane for each sample was then plotted (See FIG. 8).

From the data it is clear that the Sample 1 and Sample 13 are superior in terms of in vitro diffusion properties. These are the formulations with the same ratio of second discontinuous phase to first discontinuous phase but mineral oil versus dimethicone. Sample 15 (no second discontinuous phase) is significantly inferior to both Sample 1 and Sample 13 showing that the presence of the secondary oil phase produces a significant improvement in permeation. However, Sample 14 shows that excessive amounts of the second discontinuous phase can have a detrimental effect in terms of in vitro diffusion. Thus, there is an optimum level of the second discontinuous phase that maximises in vitro diffusion of the formulation.

Moreover, it is notable that there is no statistically significant difference between the results for Samples 1 and 13. Dimethicone is likely to have far less potential for mixing with the API oil phase on application, because dimethicone is known to have lower miscibility with other oils compared to mineral oil. The lack of a statistically significant difference between Samples and 13 therefore suggests that the improved permeation over the single API oil phase system (Sample 15) is not primarily due to a mixing of the oils on application causing an alteration in the saturation of the tacrolimus in the resulting mix.

EXAMPLE 6

Various simplified formulations were prepared using different levels of water-miscible liquid (Transcutol P™) in the aqueous phase.

| Ingredient | % wt/wt |
|---|---|
| Oil phase | |
| Tacrolimus | 0.13 |
| Capric/caprylic trigicerides | 12.73 |
| Diisopropyl adipate | 6.36 |
| Isopropyl myristate | 6.36 |
| Butylated hydroxytoluene | 0.13 |
| Aqueous phase | |
| Phenoxyethanol | 0.89 |
| Sodium citrate | 0.209 |
| Citric acid | 0.121 |
| Transcutol P ™ | x |
| Water | q.s. (to 100) |

(Transcutol P ™ = diethylene glycol monoethyl ether)

No surfactant was incorporated. This ensured that the oil phase and the aqueous phase could be vigorously mixed but would readily separate on standing overnight to make sampling and analysis more straightforward. Moreover, no mineral oil phase or gellant was included, again to make the sampling and analysis more straightforward.

The formulations were prepared by mixing the two phases with vigorous shaking by hand. They were then left to settle overnight before the oil phase was pipetted off. The two phases were centrifuged and analysed for tacrolimus using the HPLC method described herein.

The samples prepared and their associated tacrolimus (API) recovery levels are shown in the following table:

| Sample | x/wt % | API % in oil phase | API % in aqueous phase | Total recovered API |
|---|---|---|---|---|
| 16 | 0 | 97.7 | 0.09 | 97.7 |
| 17 | 5 | 96.5 | 0.20 | 96.7 |
| 18 | 10 | 95.8 | 0.95 | 96.8 |
| 19 | 20 | 91.5 | 9.24 | 100.8 |

It can be seen from the table that the higher the level of polar non-aqueous solvent incorporated to the aqueous phase, the greater the extent of the partitioning of the tacrolimus to the aqueous phase. This increased aqueous exposure is thought to explain, in part, the chemical stability trends observed in Example 1.

EXAMPLE 7

A further composition was prepared using sodium benzoate as the preservative instead of phenoxyethanol.

|  | Component | Sample 20 |
|---|---|---|
| Tacrolimus hydrate | 3 | 0.10 |
| Mineral Oil | 2 | 20.00 |
| Capric/caprylic triglycerides - Miglyol 812 ™ | 3 | 10.00 |
| Diisopropyl adipate | 3 | 5.00 |
| Isopropyl myristate | 3 | 5.00 |
| Carbomer - Ultrez 10 ™ | 4 | 1.00 |
| Laureth 4 | 2&3* | 0.40 |
| Sodium benzoate | 5 | 0.20 |
| Hydroxyethyl cellulose - Natrosol 250L ™ | 4 | 0.20 |
| Sodium citrate | 4 | 0.164 |
| Butylated hydroxytoluene | 3 | 0.10 |
| Citric acid | 4 | 0.095 |
| Polysorbate 20 | 1 | 0.04 |
| Sodium hydroxide (20% aqueous solution) | 6 | q.s. |
| Water | 1, 4, 5 (6 if required) | q.s. |
| Total |  | 100.00 |

*The substance is split in proportion betweeen the two phases depending on the relative size of the phases. For example, if the two oil phases are of the same mass, an equal mass of surfactant is added to each oil phase. If the first oil phase has twice the mass of the second oil phase, the surfactant is split in a 2:1 ratio by mass between the two phases.

Key to Components

1) Dispersion aqueous phase
2) API Non-solvent oil phase
3) API solvent oil phase
4) Gel/thickener
5) Preservative
6) pH/water adjustment The components are made separately before being sequentially added whilst undergoing suitable stirring. Components 1-3 in combination formed 50 wt % of the final formula in each case, component 4 formed 43 wt %, component 5 formed 5 wt % and and component 6 formed 2 wt %.

EXAMPLE 8

A local tolerability study in minipigs was conducted to assess the local tolerance to two topical tacrolimus creams in accordance with the present invention and a commercially available ointment, and to determine the amount of tacrolimus in the skin after twice daily administration by dermal application to minipigs for 4 weeks.

Method

Four (4) male Göttingen Minipigs were used in study. Eight (8) application sites each measuring 2.5×2.5 cm were tattooed on the back of each animal, and each formulation Sample 1 vehicle, Sample 1 with 0.03% tacrolimus, Sample 1 with 0.1% tacrolimus and Protopic® 0.1% tacrolimus ointment were applied in two different application sites on each animal.

The animals were dosed according to the schedule below.

| Treatment | Dose (mg API/animal/app. site) | Total daily dose (mg API/animal/day) | Dose (mg API/cm$^2$) | No. animals |
|---|---|---|---|---|
| Sample 21 (Vehicle - identical to Sample 1 bit without tacrolimus) | 0.0 | 0.0 | 0 | 4 |
| Sample 22 (identical to Sample 1 but containing 0.03% tacrolimus) | 0.047 | 0.188 | 0.0075 |  |
| Sample 1 (containing 0.1% tacrolimus) | 0.156 | 0.625 | 0.025 |  |
| Protopic ® 0.1% | 0.156 | 0.625 | 0.025 |  |

The following were evaluated: mortality, clinical signs, body weight and necropsy with macroscopic observations of treated and untreated skin and histopathology. Skin biopsies for bioanalysis were collected on Day 28, 4 hours after the first dosing, and at necropsy. Furthermore, application sites were examined for reaction to treatment and scored for erythema, oedema and other dermal reactions.

Biopsies were taken for bioanalysis from all application sites 4 hours+/−10 minutes after the first dosing on the last day of dosing (Day 28) and at necropsy. At each sampling time, two (one for back-up purposes) biopsies from each application site were taken. In total 16 biopsies from each animal at each sampling time. The biopsies were taken approximately 5 mm from the edges of the application sites. Prior to collection of the skin samples, the stratum corneum was separated from the skin in the part of the application site, where the biopsies were taken, by 40 strippings per two biopsies, using a commercial adhesive tape.

The biopsies were collected using a punch with a diameter of 5 mm. From the biopsies the epidermis was separated from dermis in the best possible manner using a scalpel. Following this, subcutaneous tissue was removed from the dermis using a scalpel, and then discarded. The biopsies were weighed and immediately snap frozen using liquid nitrogen and stored at −80° C. or below until analyses. Tissue samples were analysed for levels of tacrolimus using a validated bioanalytical assay.

Results

Four weeks of twice daily dermal application of topical tacrolimus creams to minipigs at three different formulations; Sample 21 (vehicle), Sample 22 (0.03% tacrolimus), Sample 1 (0.1% tacrolimus) and Protopic® 0.1% ointment were well tolerated and no test item related skin reactions or histopathological changes were observed.

The bioanalytic analysis showed that the test items were primarily located in epidermis and only a lesser content was found in dermis. Levels of tacrolimus were approximately three times higher after treatment with Sample 0.1% tacrolimus cream than after treatment with Sample 1 0.03% tacrolimus cream, indicating a dose-response relationship. Protopic® 0.1% tacrolimus ointment treatment resulted in exposure levels approximately 30% lower than Sample 1 0.1% tacrolimus cream treatment. It can therefore be concluded that, at a given tacrolimus loading, the compositions of the present invention exhibit improved skin penetration in vivo than than existing ointment formulations such as Protopic™. The data are summarized in the Table below.

TABLE

Level of tacrolimus measurable in minipig skin biopsies after twice daily application of test products for 28 days

| Test Product | Time point | Dermis (ng API/g tissue) | Epidermis (ng API/g tissue) | Total Skin (ng API/g tissue) | Ratio to Protopic (Total skin) |
|---|---|---|---|---|---|
| Sample 22 (0.03% tacrolimus cream) | Day 28, 4 h post last dosing | 62.5 | 3100 | 763 | 0.4 |
| Sample 1 (0.1% tacrolimus cream) | | 266 | 9560 | 2610 | 1.5 |
| Protopic 0.1% tacrolimus ointment | | 180 | 6240 | 1740 | 1.0 |
| Sample 22 (0.03% tacrolimus cream) | Necroscopy, 14 h post last dosing | 91.9 | 1950 | 539 | 0.4 |
| Sample 1 (0.1% tacrolimus cream) | | 197 | 6650 | 1740 | 1.3 |
| Protopic 0.1% tacrolimus ointment | | 113 | 5440 | 1340 | 1.0 |

EXAMPLE 9

An in vivo experiment using an allergic contact dermatitis model in Landrace swine (eight female pigs) was undertaken to compare dose-response of a commercially available tacrolimus ointment to compositions in accordance with the present invention containing different strengths of tacrolimus. The following test formulations were compared: Protopic™ (0.1% tacrolimus ointment), Protopic™ (0.03% tacrolimus ointment), 0.01% tacrolimus ointment, 0.003% tacrolimus ointment, Sample 1 (containing 0.1% tacrolimus), Samples 21 and 22 (identical to Sample 1 but containing no tacrolimus and 0.03% tacrolimus respectively), and Sample 23 (identical to Sample 1 but containing 0.01% tacrolimus) and Sample 24 (identical to Sample 1 but containing 0.003% tacrolimus). The 0.01% and 0.003% tacrolimus ointments were prepared in accordance with Example 1 of EP1093371B1 (using the method disclosed in Example 1 of EP-A-0474126) with the amounts of tacrolimus reduced appropriately.

The method involved administering Dinitrofluorobenzene (DNFB) and Dinitrochlorobenzene (DNCB) to skin patches to induce contact hypersensitivity, followed by treatment with one of the test formulation.

The method is based on the protocol described in Mollison et al. J Invest Dermatol. 1999 May; 112(5):729-38: a macrolactam inhibitor of T helper type 1 and T helper type 2 cytokine biosynthesis for topical treatment of inflammatory skin diseases.

Method

Day 0: Application of 100 µl of 10% Dinitrofluorobenzene (DNFB) in acetone/DMSO/olive oil (45/5/50 v/v/v) to the each of the outer aspects of both entire ears and bilateral sites on the lower abdomen≈20 cm².

Day 3: Application of 100 µl of 5% Dinitrofluorobenzene (DNFB) in acetone/DMSO/olive oil (45/5/50 v/v/v) to the internal pinnae of both ears patches and to bilateral sites on the lower thorax≈20 cm².

Day 9: Application of 60 µl of 0.6% Dinitrochlorobenzene (DNCB) in acetone/olive oil (95/5 v/v) to 18 rectangular test areas—9 on each side of the pig (3.5×3.5 cm, 12.25 cm²).

Day 9+30 minutes and 6 hours: Application of 60 µl of test formulations to test areas (3.5×3.5 cm, 12.25 cm²).

Scoring and then reapplication of test formulations was undertaken after 24 and 30 hours after the initial application of the test formulation. Erythema scoring was undertaken after 24 and 48 hours.

The test areas were scored as follows for erythema resulting from allergic contact dermatitis:
0—no erythema
0.5—questionable erythema
1—faint or scattered erythema
2—moderate erythema without induration
3—strong erythema with focal areas of edema or induration
4—extreme erythema with uniform induration or edema Results

|  | Dosage form | 24 hours | SD | 48 hours | SD |
| --- | --- | --- | --- | --- | --- |
| Protopic (0.1% tacrolimus) | Ointment | 1.7 | 0.5 | 1.0 | 0.3 |
| Protopic (0.03% tacrolimus) | Ointment | 1.9 | 0.3 | 1.1 | 0.5 |
| 0.01% tacrolimus | Ointment | 2.1 | 0.5 | 1.2 | 0.3 |
| 0.003% tacrolimus | Ointment | 2.0 | 0.5 | 1.3 | 0.4 |
| Sample 1 (0.1% tacrolimus) | Cream | 1.3 | 0.3 | 0.7 | 0.2 |
| Sample 22 (0.03% tacrolimus) | Cream | 1.5 | 0.4 | 0.9 | 0.3 |
| Sample 23 (0.01% tacrolimus) | Cream | 1.8 | 0.3 | 0.9 | 0.3 |
| Sample 24 (0.003% tacrolimus) | Cream | 1.7 | 0.4 | 1.0 | 0.2 |
| Sample 25: vehicle | Cream | 1.8 | 0.5 | 1.0 | 0.3 |

The results at 24 hours are also shown in FIG. 9 (error bars indicate standard deviation). The following conclusion was drawn for the study with Sample 1 and tacrolimus ointment:

1. Apparently, there was no effect of the lowest tacrolimus concentrations (0.003% and 0.01%) neither in the cream samples, nor in the ointment variants
2. The baseline is lower for the cream samples in accordance with the present invention than for the ointments suggesting the cream vehicle may have an independent beneficial effect on the inflammation compared to the ointment
3. A dose response trend is observed for anti-inflammatory effect of tacrolimus in the compositions of the claimed invention, and is comparable to tacrolimus in the ointment variants.

The foregoing detailed description has been provided by way of explanation and illustration, and is not intended to limit the scope of the appended claims. Many variations in the presently preferred embodiments illustrated herein will be apparent to one of ordinary skill in the art, and remain within the scope of the appended claims and their equivalents.

The invention claimed is:

1. A composition for topical application comprising: a first discontinuous phase comprising diisopropyl adipate and tacrolimus;
    a second discontinuous phase comprising mineral oil; and
        a continuous aqueous phase;
        wherein the tacrolimus is substantially soluble in the diisopropyl adipate and substantially insoluble in the mineral oil;
        wherein the phases are physically and chemically distinct;
        wherein the composition comprises less than 1 wt % surfactant by weight of the composition;
        wherein the composition comprises less than 5 wt % by weight of the composition of $C_1$-$C_4$ alcohols, polyethylene glycol, ethylene glycol, propylene glycol, butylene glycol, pentylene glycol, glycerol, diethylene glycol mono ethyl ether, propylene carbonate and mixtures of two or more thereof; and
        wherein the composition is in the form of a lotion or cream.

2. The composition according to claim 1, wherein the composition has a weight ratio of the second discontinuous phase to the first discontinuous phase of from 1:3 to 3:1.

3. The composition according to claim 1, wherein the composition comprises from 10 to 30 wt % of the second discontinuous phase by weight of the composition.

4. The composition according to claim 1, wherein the composition comprises at least 10 wt % water by weight of the composition.

5. The composition according to claim 1, wherein the composition comprises at most two discontinuous phases.

6. The composition according to claim 1, wherein the composition has a mean droplet diameter of from 1 to 30 µm.

7. The composition according to claim 1, wherein the composition has a pH of from 3.5 to 6.

8. The composition according to claim 1, wherein the composition is stable for at least 12 months at 25° C.±2° C., as measured at 60% RH±5%; and/or wherein the composition is stable for at least 6 months at 40° C.±3° C., as measured at 60% RH±5%.

9. The composition according to claim 1 for use in the treatment of human and/or animal skin by topical application.

10. A method of manufacturing a composition for topical application, the method comprising:
    (i) providing a first oil comprising diisopropyl adipate and tacrolimus;
    (ii) providing a second oil comprising mineral oil;
    (iii) providing an aqueous component; and
    (iv) dispersing the first oil and the second oil in the aqueous component to form a composition for topical application;
    wherein the first oil is different from the second oil;
    wherein the composition comprises a first discontinuous phase comprising the first oil, a second discontinuous phase comprising the second oil, and a continuous phase comprising the aqueous component;
    wherein the tacrolimus is substantially soluble in the first oil and substantially insoluble in the second oil; and
    wherein the phases are physically and chemically distinct;
    wherein the composition comprises less than 1 wt % surfactant by weight of the composition;

wherein the composition comprises less than 5 wt % by weight of the composition of $C_1$-$C_4$ alcohols, polyethylene glycol, ethylene glycol, propylene glycol, butylene glycol, pentylene glycol, glycerol, diethylene glycol mono ethyl ether, propylene carbonate and mixtures thereof; and wherein the composition is in the form of a lotion or cream.

11. The composition according to claim 1, having a total surfactant content of less than 0.5 wt % by weight of the composition.

12. The composition according to claim 1, comprising less than 1 wt % by weight of the composition of $C_1$-$C_4$ alcohols, polyethylene glycol, ethylene glycol, propylene glycol, butylene glycol, pentylene glycol, glycerol, diethylene glycol mono ethyl ether, propylene carbonate and mixtures thereof.

13. The composition according to claim 1, comprising less than 0.5 wt % by weight of the composition of $C_1$-$C_4$ alcohols, polyethylene glycol, ethylene glycol, propylene glycol, butylene glycol, pentylene glycol, glycerol, diethylene glycol mono ethyl ether, propylene carbonate and mixtures thereof.

14. The composition according to claim 1, wherein the composition has a weight ratio of the second discontinuous phase to the first discontinuous phase of from 2:3 to 3:2.

15. The composition according to claim 1, wherein the composition comprises from 15 to 25 wt % of the second discontinuous phase by weight of the composition.

16. The composition according to claim 1, wherein the composition comprises at least 50 wt % water by weight of the composition.

17. The composition according to claim 1, wherein the composition has a mean droplet diameter of from 1 to 20 µm.

18. The composition according to claim 1, wherein the composition has a pH of from 4 to 5.5.

* * * * *